(12) United States Patent
Nikolsky et al.

(10) Patent No.: US 9,353,415 B2
(45) Date of Patent: May 31, 2016

(54) METHODS FOR FUNCTIONAL ANALYSIS OF HIGH-THROUGHPUT EXPERIMENTAL DATA AND GENE GROUPS IDENTIFIED THEREFROM

(75) Inventors: Yuri Nikolsky, Del Mar, CA (US); Andrej Bugrim, New Buffalo, MI (US); Tatiana Nikolskaya, Portage, IN (US)

(73) Assignee: Thomson Reuters (Scientific) LLC, Philadelphia, PA (US)

( * ) Notice: Subject to any disclaimer, the term of this patent is extended or adjusted under 35 U.S.C. 154(b) by 1145 days.

(21) Appl. No.: 12/520,441

(22) PCT Filed: Dec. 19, 2007

(86) PCT No.: PCT/US2007/026014
§ 371 (c)(1),
(2), (4) Date: May 13, 2010

(87) PCT Pub. No.: WO2008/079269
PCT Pub. Date: Jul. 3, 2008

(65) Prior Publication Data
US 2010/0216660 A1    Aug. 26, 2010

Related U.S. Application Data

(60) Provisional application No. 60/875,648, filed on Dec. 19, 2006.

(51) Int. Cl.
*C12P 19/34* (2006.01)
*C12Q 1/68* (2006.01)

(52) U.S. Cl.
CPC ............... *C12Q 1/6886* (2013.01); *C12P 19/34* (2013.01); *C12Q 1/68* (2013.01); *C12Q 2600/112* (2013.01); *C12Q 2600/118* (2013.01); *C12Q 2600/158* (2013.01)

(58) Field of Classification Search
CPC .................................. C12P 19/34; C12Q 1/68
USPC .................................................. 435/6.1, 91.2
See application file for complete search history.

(56) References Cited

U.S. PATENT DOCUMENTS

| 5,474,796 | A | * | 12/1995 | Brennan | 427/2.13 |
| 6,054,270 | A | * | 4/2000 | Southern | 435/6.12 |
| 7,514,209 | B2 | * | 4/2009 | Dai et al. | 435/6.14 |
| 2007/0038385 | A1 | | 2/2007 | Nikolskaya et al. | |
| 2007/0219768 | A1 | | 9/2007 | Ekins et al. | |

FOREIGN PATENT DOCUMENTS

WO    WO-2006/103442    10/2006

OTHER PUBLICATIONS

International Preliminary Report on Patentability for PCT/US2007/26014, issued on Jun. 24, 2009, 5 pages.
International Search Report for PCT/US2007/26014, mailed on Sep. 19, 2008, 3 pages.
Lu et al., Breast Cancer Res. Treat. (2008) 108:191-201.
"GeneChip Human Genome U133 Set" http://www.affymetrix.com/support/technical/datasheets/hgu133_datasheet.pdf, retrieved on Feb. 26, 2003.
Ivshina et al., Cancer Research (2006) 66(21):10292-10301.
Jongwoo Song, "A sequential clustering algorithm with applications to gene expression data" Ph.D. Dissertation, University of Chicago, Aug. 2003.
Nikolsky et al., Proceedings of the Annual Meeting of the American Association for Cancer Research (2007) 48:282.
Sorlie et al., BMC Genomics (2006) 7:127.
Sotiriou et al., PNAS USA (2003) 100(18):10393-10398.
Supplementary European Search Report for EP 07 86 3157, mailed on Dec. 4, 2009, 10 pages.
Teschendorff et al., Bioinformatics (2006) 22(18):2269-2275.
Wang et al., Lancet (2005) 365:671-679.
Yu et al., Cancer Research (2004) 64(9):2962-2968.

* cited by examiner

*Primary Examiner* — Samuel Woolwine
*Assistant Examiner* — Olayinka Oyeyemi
(74) *Attorney, Agent, or Firm* — Morrison & Foerster LLP

(57) ABSTRACT

The present invention relates generally to groups of genes that can be used to diagnose and differentiate between types of specific diseases such as breast cancer. The groups of genes can be further used to develop diagnostic kits for the specific diseases. The diagnostic kits can also differentiate between sub-categories of a disease to help identify the appropriate treatment regimen for a patient.

1 Claim, 29 Drawing Sheets

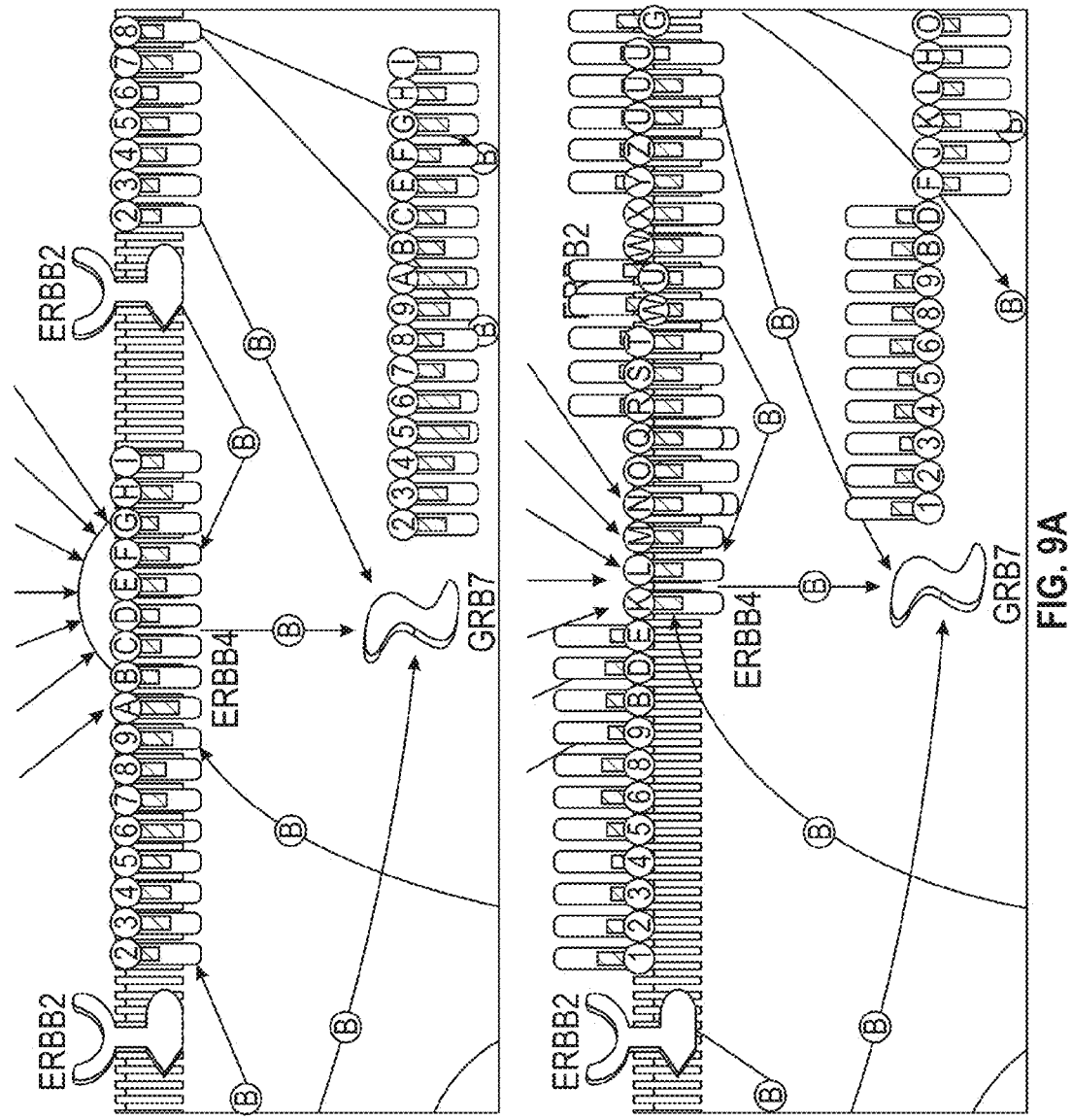

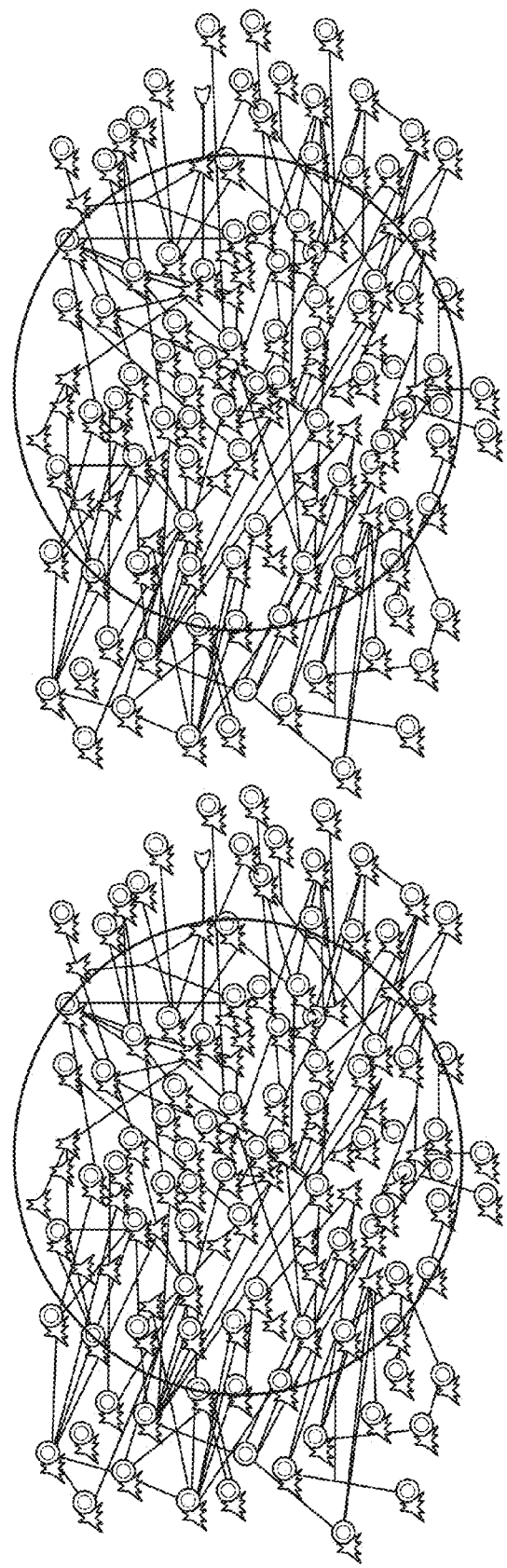

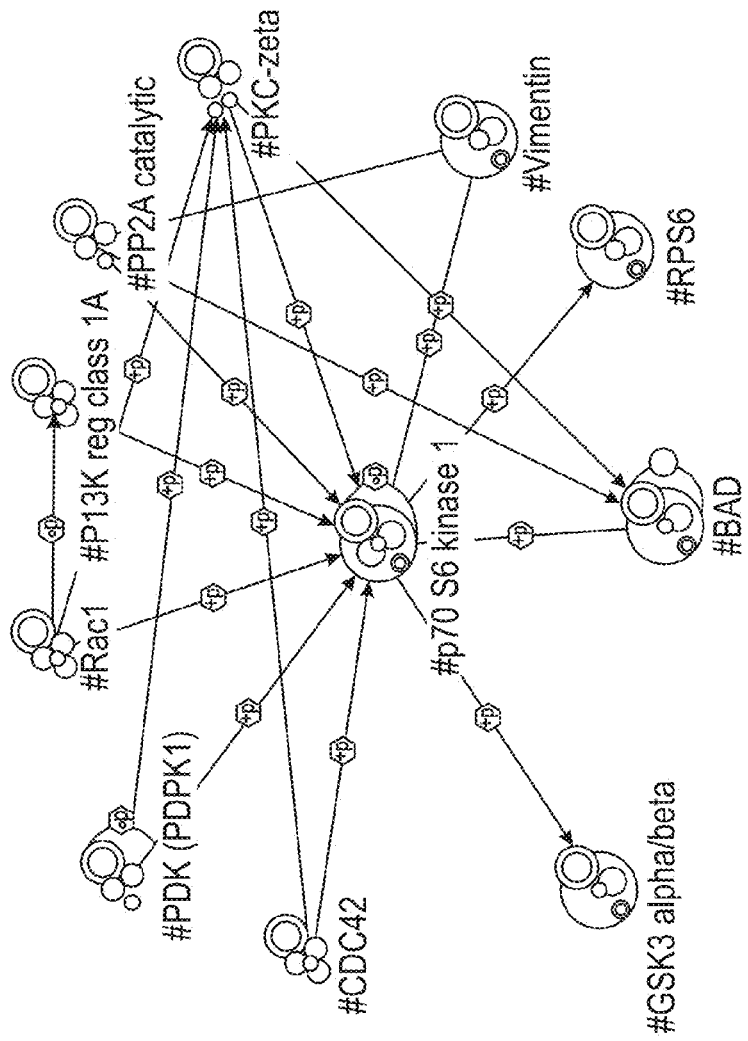
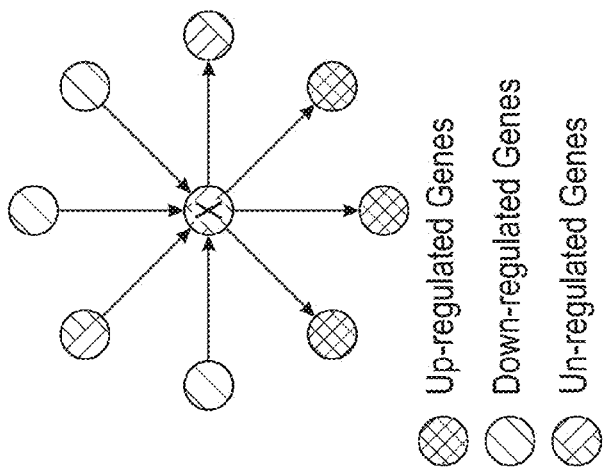
FIG. 18B
FIG. 18A

METHODS FOR FUNCTIONAL ANALYSIS OF HIGH-THROUGHPUT EXPERIMENTAL DATA AND GENE GROUPS IDENTIFIED THEREFROM

CROSS-REFERENCE TO RELATED APPLICATIONS

This application is the national phase of PCT application PCT/US2007/026014 having an international filing date of Dec. 19, 2007, which claims priority from provisional application No. 60/875,648 filed Dec. 19, 2006. The entire contents of these documents are incorporated herein by this reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 655202000600SeqList.txt, date recorded: Jan. 7, 2016, size: 17,061 bytes).

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of Invention

The present invention relates generally to compositions and methods of identifying groups of genes that can be used to differentiate between types of specific diseases such as breast cancer.

2. Description of Related Art

Sequential clustering method. The methods of high-throughput (HT) biology deeply impact disease research, particularly such heterogeneous and complex conditions as breast cancer. The rate of progress in OMICs technologies, data interpretation and applications is increasing. Over the last 2-3 years, a set of novel methods of functional analysis of large datasets (often collectively referred to as systems biology) have advanced into practice. After years of development "below the radar screen" of wet lab research, the data mining methods based on biological networks and pathways analysis, are now being applied in disease studies. However, despite impressive progress in research, the results and methods of HT biology have not yet advanced into clinics.

Global gene expression profiling in breast cancer. The second deadliest malignancy in Western women, breast cancer is a complex disease (or rather a collective "condition" describing a diverse set of disease states) which involves many tissues and cell subtypes. A large scope of factors is believed to contribute to the clinical manifestations such as survival, response to therapy, relapsing time, and risk factors for metastases. Breast cancer is diagnosed by imaging, there are no diagnostic DNA and/or protein markers used. It is now recognized that breast cancer cannot be properly classified with any single gene/protein/phenotype descriptor, and multiple gene/protein markers are needed in order to capture the complexity of the disease. The logistics for such multi-factorial analysis was provided by robust microarray and Systematic Analysis of Gene Expression (SAGE) technologies, and a number of large scale studies of "genome wide" expression profiling of breast tumors were conducted in the last 10 years. The two most clinically important issues addressed were the sub-categorization of cancers and the discovery of prognostic signatures for distant metastasis—the predominant cause of mortality due to breast cancer Sub-categorization of breast cancers. One of the best known studies in molecular profiling is the series of works on clustering of invasive breast cancers by T. Sørlie et al. The studies were carried out on cDNA arrays developed in Patrick Brown's lab at Stanford on large samples sets; are well documented and directly comparable within series. First, distinct patterns for basal and luminal epithelium, stroma and lymphocytes were identified as intrinsic "signatures" unique for tumors. In the follow-up studies, 122 tissue samples (including 115 invasive breast carcinomas, 4 normal breast samples) were tested by two dimensional non-supervised hierarchical clustering of the "centroid" set of 540 genes. The expression patterns in tumors followed the signatures for particular cell lines: two types of luminal epithelium (A and B), basal epithelium, normal-like and ERBB+ clusters. The Luminal A type was characterized by high expression of estrogene receptor (ER) and several of its target genes LIV-1, HNF3A, XBP1 and GATA3. Luminal B type featured lower ER expression, and high expression of GGH, LAPTMB4, NCEP1 and CCNE1. The characteristic set for basal-like type included keratins 5 and 17, annexin 8, CX3CL1 and TRIM29. Basal type was ER negative and lacking expression of luminal a genes. Finally, the ERBB+ cluster featured high expression of some genes from ERBB amplicon: ERBB2, GRB7, TRAP100. The normal-like type had an expression pattern of adipose and other non-epithelial cell types. This clustering schema proved to be largely correct in another study on the same cDNA array on the set of 295 patients, and independent data-sets on different microaray platforms. In a more recent study, a different cluster, called "molecular apocrine" characterized as androgen receptor (AR) positive, ER negative group outside basal category, characterized by frequent ERBB2 amplification. Importantly, clinical phenotypes correlated with particular clusters. For instance, the basal and ERBB+ subtype were associated with the shortest patients survival time. However, despite robustness and usefulness in research and clinics, this "classic" sub-categorization schema is incomplete and suffers drawbacks. First, about ⅓ samples could not be parsed in any of 5 categories in both the 122 samples set and 295 samples sets. Such a high rate of unclassifiable patients limits the applicability of microarray clusters in clinic. Second, the clusters remain heterogeneous. These drawbacks pursued us to develop a radically different classification approach described in this application.

Functional analysis of global gene expression and other OMICs data. With thousands of data points and whole-genome representation, OMICs datasets undergo rigorous statistical analyses such as evaluation of significance of data points, supervised and unsupervised clustering, analysis of variance ANOVA, principal component analysis (PCA) and other tests). However, statistical analysis is insufficient for interpretation the "underlying biology" behind expression profiles. Typically, functional analysis of gene expression is limited to querying the statistically derived gene lists against cellular process ontologies such as GO. This is informative for "big picture" observations, for instance for association of a metastasis signature with "cell death, cell cycle, proliferation and DNA repair". However, the resolution is inadequate for "fine mapping" of the dataset at the level of individual protein interactions and for revealing the combinations of biological events causative of the condition. We consider the major tools for data analysis as pathways, cellular processes and networks (signaling and metabolic). Pathways represent the linear chains of consecutive biochemical transformations or signaling protein interactions, experimentally confirmed as a whole. Functional processes are the folders, or categories, with proteins needed for execution of distinct cellular functions, such as apoptosis or fatty acids oxydation. Unlike pathways, the proteins within processes are not connected by functional links. Both pathways and process categories are static, i.e. experimental data can be mapped (via linking data points IDs) on the pathways and processes, but not alter them. Biological networks are essentially different. They represent combinations of objects—nodes (proteins, metabolites, genes etc.) interconnected by links (binary physical protein interactions, single step metabolic reactions, functional correlations) and assembled "on the fly" from the interaction tables. Biological networks are dynamic, as they are built de novo out of building blocks (binary interactions) and are specific for each dataset. A combination of networks, "interactome", is probably the closest representation of the "cellular machinery" of active proteins which carry out cellular functions The complete set of interactions defines the potential of core cellular machinery, billions of physically possible multi-step combinations. Obviously, only a fraction of all possible interactions are activated at any given condition as not all genes are expressed at a time in a tissue, and only a fraction of the cellular protein pool is active. The subset of activated (or repressed) genes and proteins is unique for the experiment, and is captured by data "snapshots" such as microarrays. Once generated, the network(s) can be interpreted in terms of higher level processes, and the mechanism of an effect can be unraveled. This is achieved by linking the network objects to Gene Ontology (GO) and other process ontologies, as well as metabolic and signaling maps. The process of data analysis consists of narrowing down the list of potentially many thousands of data points to small sets of genes, interconnected functionally and most affected in the condition. This is achieved by using scoring methods for the intersections between functional categories, and calculation of the relevance to the dataset in question (relative saturation of pathways and networks with the data).

Unforeseen toxicity of new compounds in human is one of the leading reasons for drug withdrawal from the market and from clinical trials. A recent analysis of drugs entering pre-clinical studies suggested that between 2000 and 2002 only one of 13 molecules entering clinical studies reached the market. This and other studies together indicate that the cost for developing a drug including marketing is increasing and could be in excess of $1 billion. The inability to predict toxicity cost the pharmaceutical industry an estimated $8 billion in 2003. The critical significance of the drug failure problem created a steadily growing market for novel predictive technologies, such as toxicogenomics (assessment of compound toxicity in human based on pre-clinical molecular profiling) and pharmacogenomics (evaluation of individual susceptibility to drug efficacy and side effects based on genotype). The majority of toxicogenomic studies are drug-effect experiments on rat and mouse models, typically genome-wide gene expression profiling using a microarray platform. Current analytical software and empirical gene expression reference databases include Iconix DrugMatrix and GeneLogic's ToxExpress. This software has relatively low predictive power. However, this situation may drastically change with the development of the next generation tools for functional analysis and systems biology.

Microarrays provide a snapshot of the gene expression of thousand of genes in a given time and condition, one of the major challenges being to identify genes or groups of genes associated with different disease conditions. Most of the methods have been developed to identify significant changes in the expression levels of individual genes, however the expression changes can be experienced in the level of pathways or functionally related network modules. There is less work focusing on the simultaneous use of gene expression and interaction information. Related studies include identifying biologically active sub-networks of networks by using scoring functions of the sub-networks and other approaches focuses on gene expression changes of a pre-defined set of genes which are known to be biologically related. Our approach is similar in nature, focusing on identifying from pre-defined network modules the ones, which differentiate between any two treatment-conditions, i.e. they are characterized by an expression pattern which changes in a synchronous manner over the different treatment conditions Traditional methods based on the expression changes of individual genes are unable to identify these relatively small but simultaneous expression pattern changes.

OMICs-based approaches in mechanistic toxicology. Regulatory assessment of potential toxicant hazards is mandated for both food and drug compounds (FDA) and for industrial chemicals and commercial compounds that will be released into the environment (EPA). For both of these broad categories, risk assessment of toxicity from chemical or drug exposure is comprised of two related processes: hazard characterization and exposure assessment. It is widely accepted that a mechanistic understanding of the interaction of chemicals and living systems is required for a full evaluation of drug and chemical safety. The majority of 'OMICs-based studies of mechanisms of chemical toxicity (toxicogenomics) are focused on transcriptional gene expression profiling and proteomic and metabolomic profiling methods are currently being developed to provide a comprehensive view of the toxicant response. Molecular profiling approaches are being increasingly integrated into pre-clinical drug safety evaluation and into clinical studies of toxicant-related disease. The underlying assumption behind toxicogenomics is that chemicals with similar mechanisms of toxicity will evoke similar patterns of gene expression in the affected target tissue. Therefore potential toxicity of a compound may be determined by a comparison of its gene expression pattern with a library of standardized expression patterns for xenobiotics with known toxicity. The liver and kidney are primary sites of xenobiotic metabolism and consequently, hepatotoxicity or nephrotoxicity manifestations. The reference expression pattern libraries are therefore focused mostly on rat liver as this is the most extensively utilized toxicity assay system. The patterns of gene expression can be presented in a variety of ways depending on the statistical procedures applied (from a list of most affected by expression amplitude genes to neural networks). Drug expression responses are mainly presented in the form of compound or class specific "gene signatures", i.e. lists of genes (expression biomarkers) characteristic for a certain type of toxicity. Gene signatures are typically 50-100 genes strong and are diagnostic for exposure to a specific chemical with predictive power often >90%. Gene signatures are generated using different statistical techniques, such as unsupervised clustering and supervised pattern matching algorithms. The reference, compendium databases of toxicant signatures were assembled initially for yeast and subsequently for rodents.

It is well recognized by federal regulatory agencies that molecular profiling of toxicant exposure must be integrated with pathological and clinical profiling data of disease states. To support this integration for drug safety evaluation, the FDA has released a "Guidance for Industry on Pharmacogenomic Data Submissions". Similarly the Science Policy Council has prepared an "Interim Policy on Genomics" and has organized its own internal "Framework for a Computational Toxicology Research Program in ORD". Reference standards for experimental design and reporting for toxicogenomic studies have been loosely adopted as the MIAME-Tox standard. To date, no universally accepted standardized experimental platform or common database schema exists for toxicogenomic studies. At present, several public, academic, and commercial databases exist as specific repositories for toxicogenomic data (Table 1). Toxicogenomics and chemogenomics databases were instrumental in finding additional class specific gene signatures and prediction of both drug induced oxidative stress-mediated hepatotoxicity and drug induced renal tubule degeneration and nephrotoxicity.

TABLE 1

Public and Commercial Toxicogenomics Databases, Protocols and Resources

| Database | Source | Type | Array |
| --- | --- | --- | --- |
| Tox-MIAME | MGED | Protocol | N/A |
| CEBS | NCT/NIEHS/NIH | DB/public | Multiple |
| ArrayTrack | FDA | DB/public | Multiple |
| CTD | MDIBL | DB/public | |
| PharmGKB | Stanford U. | DB/academic | Multiple |
| EDGE | U. Wisconsin | DB/academics | mouse, custom |
| dbZach | Michigan State U. | DB/academic | rat, custom |
| ToxExpress | GeneLogic | DB/commercial | rat, Affymetrix |
| DrugMatrix | Iconix Pharma | DB/commercial | rat, GE |

Consequently, there is a need in the pharmacogenetics industry for effective and efficient methods for analyzing pathway databases to predict potential new drugs or treatments. Such a method could be used to evaluate proposed new drugs or treatments against the pathway databases to predict adverse and side effects that may be expected before expensive clinical trials are begun.

BRIEF SUMMARY OF THE INVENTION

In this invention, two novel complementary methods, namely the methods of sequential clustering and of signature networks, are used to perform functional analysis of high-throughput experimental data, primarily whole genome gene expression profiles. The method of sequential clustering is primarily applicable for sub-categorization of large datasets of gene expression profiles for samples of genetically heterogeneous background; a typical dataset is a multi-patient set for genetically complex human diseases, such as cancers, diabetes, obesity, cardiovascular diseases etc. The method allows splitting samples into smaller clusters with distinct expression patterns for groups of selected genes (descriptor groups). Each cluster is associated with a certain distinct genotype and clinical outcome and a certain treatment for the patients that have an expression profile belonging to a certain cluster. The sequential clustering method can be applied in drug development clinical trials and for patient's treatment in a clinic. In both cases, if the patient's gene expression profile can be classified in a particular descriptor group, then the patient's proper treatment can be determined by the particular descriptor group.

The signature network method identifies specific modules of protein and gene interactions (signature networks) that are synchronously up- or down-regulated in certain conditions such as cellular response to drug treatment. This method is primarily applicable to genetically homogenous gene expression datasets, for example pure strains of laboratory animals such as mice and rats, human and animal cell lines or genetically similar human patients. The primary application areas for the signature networks method is drug response studies (toxicogenomics, mode of action studies) and as descriptors for gene expression clusters identified by the sequential clustering method. This method is useful in preclinical and clinical drug development or drug toxicity evaluation, and in primary care as a descriptor for patients' clusters.

The function and advantage of these and other embodiments of the present invention will be more fully understood from the examples described below. The examples presented are intended to illustrate the benefits of the present invention, but do not exemplify the full scope of the invention.

BRIEF DESCRIPTION OF THE SEVERAL VIEWS OF THE DRAWINGS

The accompanying drawings are not intended to be drawn to scale. In the drawings, each identical or nearly identical component that is illustrated in various figures is represented by a line numeral. For purposes of clarity, not every component may be labeled in every drawing.

In the drawings,

FIG. 4 is a representation of bi-modal genes.

FIG. 7 is a representation of sequential clustering of the 122 patient set with seven descriptor groups.

FIG. 9A-B is a representation of mapping of the clusters samples data on the pathway maps;

FIG. 11A is a representation of the calculation of distances between samples in the pathway's gene expression space. A hypothetical pathway is shown, consisting of three proteins A, B and C. Samples are represented as points in 3-dimensional space of gene expression. Note grouping of samples. Also pathways corresponding to gene expression (fold change compared to control) are represented by arrows. FIG. 11B is a representation of clustering of samples in the pathway's gene expression space;

FIG. 16 is a representation of "Direct Interactions" (DI) networks assembled from the genes extracted from the most pathways between tamoxifen and phenobarbital profiles, FIG. 16A is a representation of "Direct Interactions" (DI) networks assembled from the genes extracted from the most pathways between tamoxifen and phenobarbital profiles. Blue circles represent down-regulated genes; red circles represent up-regulated genes.

FIG. 17 is a representation of the workflow for generating signature networks from toxicogenomics data. FIG. 17B represents the functional relatedness between gene sets that have little or no direct overlap. Gene sets A (red) and B (green) have two common genes (stripes) but all eight network edges are similar;

FIG. 18 is a representation of a statistically significant network (directed graph) neighborhood. (A) Node X features down-regulated upstream first degree neighbors (blue), and up-regulated downstream neighbors. Statistical scores for such distributions can be calculated using hyper-geometric distribution. (B) A real network example. Statistically significant distribution of down-regulated genes from allyl-alcohol induced expression profile in the neighborhood of P70 S6 kinase1. Upstream genes are predominantly down-regulated (blue). The network is built in MetaCore™ 3.0;

FIG. 19 is a representation of a comparison of drug treatment signature networks.

DETAILED DESCRIPTION OF THE INVENTION

Figure 1:
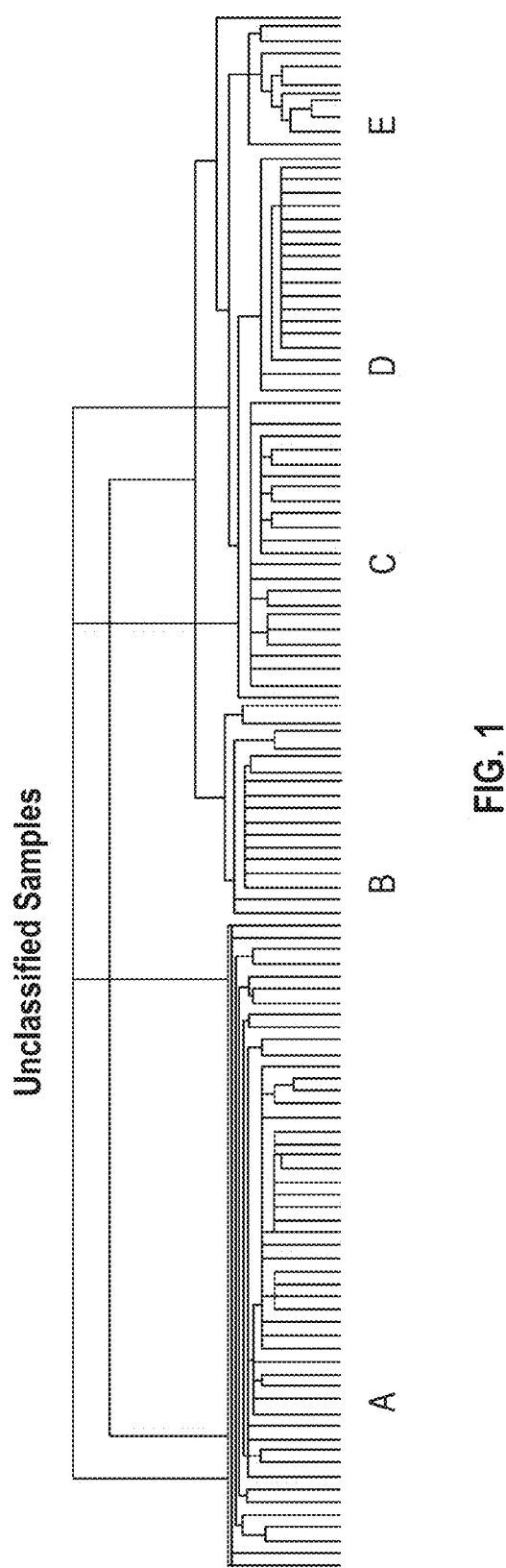
FIG. 1 is a representation of the sub-categorization of invasive breast cancers based on global expression profiling from two types of luminal epithelium (A and B, FIGS. 1A and 1B respectively); basal epithelium (FIG. 1D); normal-like (FIG. 1E); and ERBB+ clusters (FIG. 1C)

The latest challenge for the pharmacogenetics industry is to develop effective and efficient methods for analyzing pathway databases to predict potential new drugs or treatments. Alternatively, the databases may be used to evaluate proposed new drugs or treatments against the pathway databases to predict adverse and side effects that may be expected before expensive clinical trials are begun.

Regulatory assessment of potential toxicant hazards is mandated for both food and drug compounds (FDA) and for industrial chemicals and commercial compounds that will be released into the environment (EPA). For both of these broad categories, risk assessment of toxicity from chemical or drug exposure is comprised of two related processes: hazard characterization and exposure assessment. It is widely accepted that a mechanistic understanding of the interaction of chemicals and living systems is required for a full evaluation of drug and chemical safety. The majority of 'omics-based studies of mechanisms of chemical toxicity (toxicogenomics) are focused on transcriptional gene expression profiling and proteomic and metabolomic profiling methods are currently being developed to provide a comprehensive view of the toxicant response.

The underlying assumption behind toxicogenomics is that chemicals with similar mechanisms of toxicity will evoke similar patterns of gene expression in the affected target tissue. One can therefore deduce the potential toxicity of a compound by a comparison of its gene expression pattern with a library of standardized expression patterns for xenobiotics with known toxicity. The liver and kidney are primary sites of xenobiotic metabolism and consequently, hepatotoxicity or nephrotoxicity manifestations. The reference expression pattern libraries are therefore focused mostly on rat liver as this is the most extensively utilized toxicity assay system. The patterns of gene expression can be presented in a variety of ways depending on the statistical procedures applied (from a list of most affected by expression amplitude genes to neural networks). Drug expression responses are mainly presented in the form of compound or class specific gene signatures, i.e. lists of genes (expression biomarkers) characteristic for a certain type of toxicity. Gene signatures are typically 50-100 genes strong and are diagnostic for exposure to a specific chemical with predictive power often >90%. Gene signatures are generated using different statistical techniques, such as unsupervised clustering and supervised pattern matching algorithms.

In this invention, two novel complementary methods, namely the methods of sequential clustering and of signature networks, are used to perform functional analysis of high-throughput experimental data, primarily whole genome gene expression profiles.

The method of sequential clustering is primarily applicable for sub-categorization of large datasets of gene expression profiles for samples of genetically heterogeneous background; a typical dataset is a multi-patient set for genetically complex human diseases, such as cancers, diabetes, obesity, cardiovascular diseases etc. The method allows splitting samples into smaller clusters with distinct expression patterns for groups of selected genes (descriptor groups). Each cluster is associated with a certain distinct genotype and clinical outcome and a certain treatment for the patients that have an expression profile belonging to a certain cluster. The sequential clustering method can be applied in drug development clinical trials and for patient's treatment in a clinic. In both cases, if the patient's gene expression profile can be classified in a particular descriptor group, then the patient's proper treatment can be determined by the particular descriptor group.

Biological networks are generated and analyzed by the methods of modern graph theory originated in the studies of Swiss and German mathematicians in the 18th and 19th century. The "default" random network theory states that pairs of nodes are connected with equal probability and the degrees follow a Poisson distribution. This implies that it is very unlikely for any node to have significantly more edges than average. The analysis of the yeast interactome revealed that networks are remarkably non-random and the distribution of edges is very heterogeneous, with a few highly connected nodes (hubs) and the majority of nodes with very few edges. Such topology is defined as scale-free, meaning that node connectivity obeys the power law: $P(k) \sim k^{-\gamma}$. $P(k)$ is the fraction of nodes in the network with exactly k links. Interestingly, the hubs are predominantly connected to low-degree nodes, a feature that gives biological networks the property of robustness. Removal of even a substantial fraction of nodes still leaves the network connected. The non-random topology correlates with the biological properties of nodes and edges. The well-connected hubs (defined here as the top quartile of all nodes in terms of the number of edges) are largely represented by evolutionary conserved proteins because the interactions impose certain structural constraints on sequence evolution.

Network analysis is broadly applicable throughout the drug discovery and development pipeline, both on the biology and the chemistry side. Any type of data that can be linked to a gene, a protein or a compound, can be recognized by the input parsers, visualized and analyzed on the networks. Therefore, almost any pre-clinical high throughput (HT) experiment, as well as patient DNA or metabolic tests from clinical trials can be included in network analyses. Most importantly, all these different datasets can be processed on the same network backbone. Therefore, networks represent the universal platform for data integration and analysis, which has always been the major objective of bioinformatics technology. Network analysis of complex human diseases is a relatively new area.

The signature network method identifies specific modules of protein and gene interactions (signature networks) that are synchronously up- or down-regulated in certain conditions such as cellular response to drug treatment. This method is primarily applicable to genetically homogenous gene expression datasets, such as pure strains of laboratory animals for example mice and rats, human and animal cell lines or genetically similar human patients. The primary application areas for the signature networks method is drug response studies (toxicogenomics, mode of action studies) and as descriptors for gene expression clusters identified by the sequential clustering method. This method will also be useful in preclinical and clinical drug development or drug toxicity evaluation, and in primary care as a descriptor for patients' clusters.

Previously the applicants developed a novel approach to analysis of toxicogenomics data based on functional data mining tools and biological networks. The co-owned inventions are described in the pending patent applications "Methods for Identification of Novel Protein Drug Targets and Biomarkers Utilitizing Functional Networks", filed 4 Aug. 2006 and "System and Method For Prediction of Drug Metabolism, Toxicity, Mode of Action, and Side Effects of Novel Small Molecule Compounds", U.S. patent application Ser. No. 11/378,928 filed 17 Mar. 2006, which are both herein incorporated by reference in entirety.

In this invention, the two methods of sequential clustering and signature networks are then also used to identify markers for breast cancer and determining the most effective treatment based upon the markers.

Breast cancer is the deadliest malignancy in Western women and is a complex disease (or rather a collective condition characteristic for a diverse set of disease states) that involves many tissues and cell subtypes. The cancer arises as a result of an unlucky series of molecular events, which cause-consequence relationships are yet poorly understood, including germ line and somatic mutations, chromosomal instability, epigenetic changes in DNA methylation pattern, fundamental changes of gene expression and proteomics patterns. In addition to the anatomically-based tumor, nodes, metastasis (TNM) staging system for solid tumors, breast cancers are divided into five groups based on gene expression patterns; believed to be highly heterogeneous in genetic background with less than 10% tumors clearly contributable to one genetic biomarkers, BRCA I and BCRA II, and influenced by exogenous factors such as diet.

With such complex etiology, a large scope of factors is believed to contribute to the disease sub-categorization and phenotype, including prognosis, response to therapy, relapsing time, and risk factors for metastases. It is not surprising that the diagnostics and prognosis based on established DNA and protein serum markers are rather imprecise. For instance, the prognostic markers for the 10-15% of breast cancer patients develop metastases within three years since initial diagnosis, but in many cases metastases arise after 10 years. Histological typing is only a weak metastasis prognostic marker, as well as the relationships between metastases and tumor-positive axillary lymph nodes, and single gene molecular prognostic markers such as ERBB2 over-expression, status of estrogen receptor (ER), BRCA and protein level of uPA/PAI1.

It was revealed, that such high degree of heterogeneity cannot be properly described and classified with one or even a combination of single gene/protein/phenotype descriptor, and multiple gene/protein markers have to be developed in order to capture the complexity of the disease. The logistics for such multi-factorial analysis was provided by robust microarray and SAGE technologies; and a number of large-scale studies of genome-wide expression profiling of breast tumors in different aspects were conducted over the last ten years. The two most clinically important aims accessed by these studies was sub-categorization of cancers depending on expression profiles and discovery of prognostic signatures for metastases—the most important cause of mortality from the disease.

The series of works on clustering of invasive breast cancers by the group of investigators from Norwegian Radium Hospital and Stanford University lead by Therese Sørlie is one of the best known studies in microarray expression profiling. The study was conducted with several cDNA arrays based on the original glass spotted array developed 10 years ago in Patrick Brown's lab at Stanford. The studies were carried out on large sets of samples, and conducted on the same basic array platform with the same procedures. These features make the works reproducible and directly comparable. Importantly, the results are well documented and all raw data is available at Stanford Microarrays Database, which makes the data directly applicable for "meta-analysis" by other groups—a rather rare case in microarray expression.

In the first study, a set of 65 surgical specimens from 42 patients and 17 cultured cell lines was chosen for identification of clusters of co-expressed genes. The expression patterns of the cell lines were used as internal markers to correlate the co-expressed gene clusters with specific cell types within the tumors. As such, the patterns for basal and luminal epithelium, stroma and lymphocytes were identified. The clusters of synchronous expression were associated with such cellular processes as proliferation and activation of specific signal transduction pathways. Importantly, the investigators used pairs of tumors taken before and after 15-weeks long chemotherapy treatment, and the expression pattern remain remarkably consistent within pairs. Therefore, these patterns could be considered as intrinsic signatures unique for tumors.

In the follow-up studies, up to 122 tissue samples (115 from invasive breast carcinomas, 4 normal breast samples, 7 samples from non-malignant tumors) were tested. First, the intrinsic centroid gene set of 540 most relevant genes was selected from 8,000 expressed genes on the array. Next, two dimensional non-supervised hierarchical clustering was used for parsing the intrinsic set into 5 distinct clusters with characteristic genes known as biomarkers for different breast cancer onsets. The expression patterns in tumors followed the signatures for particular cell lines: two types of luminal epithelium (A and B, FIGS. 1A and 1B respectively); basal epithelium (FIG. 1D); normal-like (FIG. 1E); and ERBB+ clusters (FIG. 1C). The luminal A type was characterized by high expression of ER, LIV-1, HNF3A, XBP1 and GATA3. Luminal B type featured lower ER expression, and high expression of GGH, LAPTMB4, NCEP1 and CCNE1. The characteristic set for basal-like type included keratins 5 and 17, annexin 8, CX3CL1 and TRIM29. Basal type was ER negative and lacking expression of luminal A genes. Finally, ERBB+ cluster featured high expression of some genes from ERBB amplicon: ERBB2, GRB7, TRAP100. The normal-like type had an expression pattern of adipose and other non-epithelial cell types. Since first publication in 2001, this clustering schema was tested and proved to be largely correct with further studies on the same cDNA array on the set of 295 patients, and on independent data sets received by other groups on different microarray platforms.

Identification of prognostic gene sets for metastases development is the second major focus in expression profiling in breast cancer. The reason for such interest is poor conventional diagnostic for metastases, which are the main cause of death in any cancer. Since the likeliness of metastases development cannot be predicted at time of diagnosis, 80% patients receive adjuvant chemotherapy. Yet, only 40% of diagnosed women develop and ultimately die from metastases, and therefore, over half patients are "over-treated" with toxic chemotherapy. By now, it is widely believed that no single marker gene, expression or protein marker could be sufficient for such a complex disease group as breast cancer, and global gene expression is probably the best available technology for deriving multi-gene metastases markers. Traditional methods based on the expression changes of individual genes are unable to identify relatively small but simultaneous expression pattern changes.

The data mining process of using both sequential clustering and signature networks was tested on the sub-categorization of invasive breast cancers, based on more fundamental grounds than the unsupervised and supervised statistical clustering applied so far. First, standard data mining tools (pathways, networks, cell processes) were used to evaluate the published datasets of 122 and 295 patients with invasive cancers, but the heterogeneity between patients within clusters was prohibitively high for direct functional analysis. Therefore, the patients were divided into groups using a novel approach of sequential clustering, followed by functional analysis of the novel clusters. Applying a combination calculation of bi-modality and a novel closeness technique, two small sets of genes were identified that are characteristic for certain patients groups. Using this technique, both patient sets were divided into 18 biologically meaningful clusters, with no unclassified patients. Identification of the set of "breast cancer—specific" bi-modal genes is based on comparison of expression profiles from normal breast tissue and tumors, but none of the published studies had a sufficient number of norms.

Figure 2:
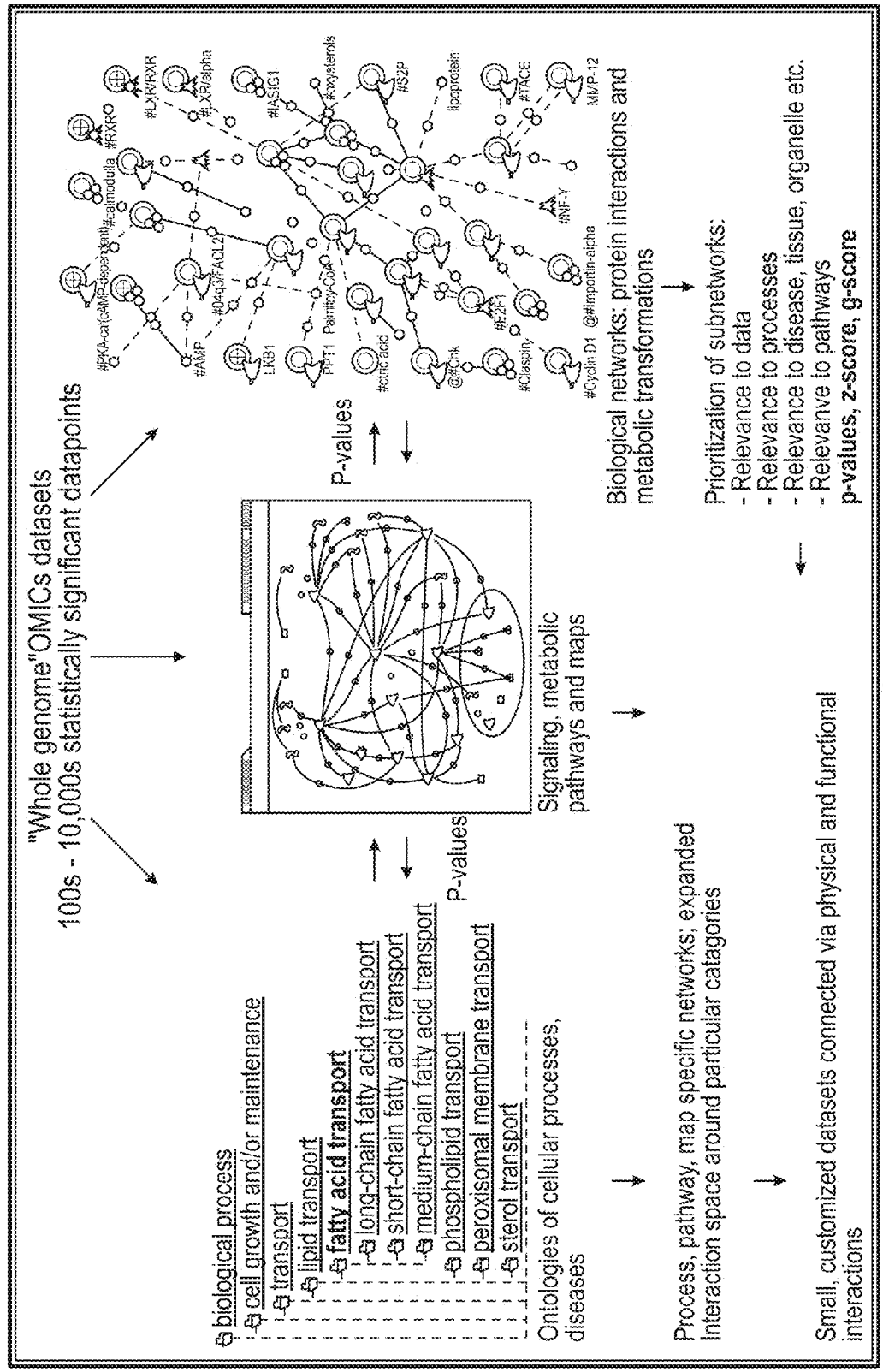
FIG. 2 is a representation of a workflow of functional analysis of proteomics and other OMICs data.
Figure 3:
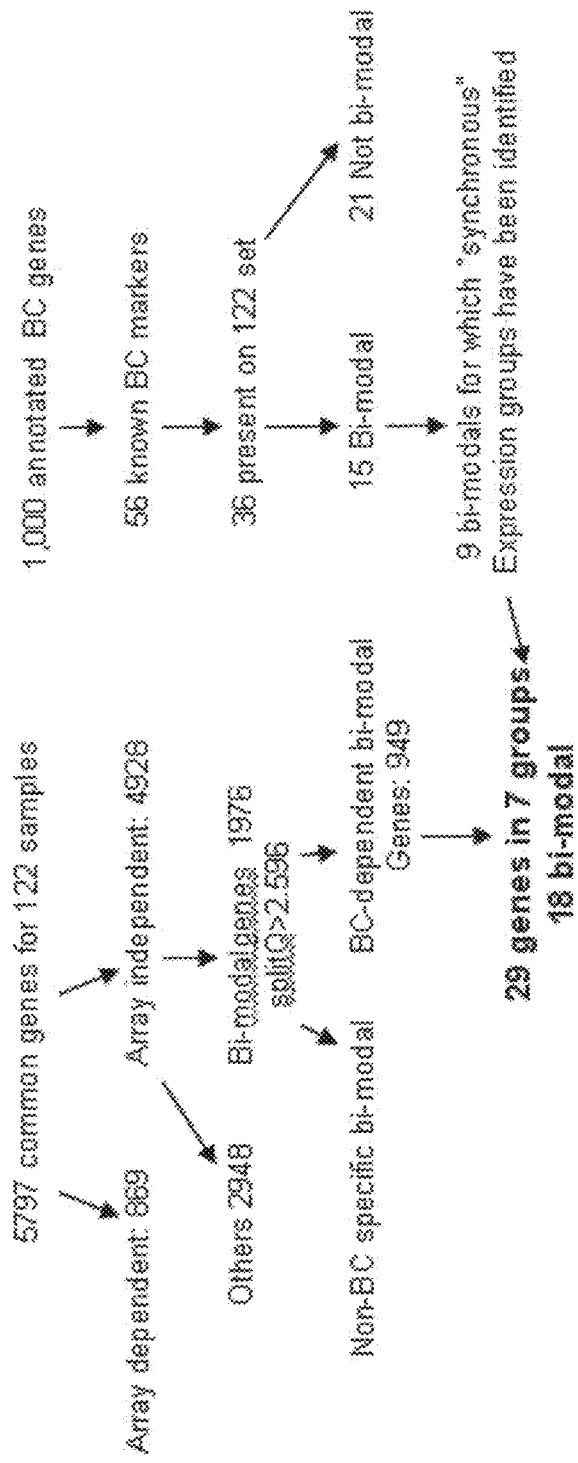
FIG. 3 is a representation of the clustering workflow described in the invention.

In the studies by Therese Sørlie described above, despite obvious robustness and usefulness in research and clinics, the traditional sub-categorization in the studies was incomplete and suffered serious drawbacks. First, about one-third of the patient datasets could not be parsed in any of five categories in both the 122 sample set and the 295 sample set; FIG. 1 is a representation of the sub-categorization of invasive breast cancers based on global expression profiling for Luminal A (FIG. 1A), Luminal B (FIG. 1B), ERBB+ (FIG. 1C), Basal (FIG. 1D), and Normal-like (FIG. 1E). Obviously, the proportion of unclassified samples is higher when applied on different microarray platforms. Such a high rate of unclassifiable patients limits the applicability of the schema in the clinic. Second, the clusters remain heterogeneous in terms of expression of many important genes from intrinsic set, which may be seen when performed functional networks and pathways analysis (FIG. 2). FIG. 2 is a representation of a workflow of functional analysis of proteomics and other OMICs data. Large datasets are mapped on canonical biological pathways, are classified in ontologies of cellular processes and are used to build condition-specific networks. Processes, pathways and networks are scored depending on relative saturation with the experimental data points, and can be prioritized relative to each other. Different statistical procedures are applied for comparing the networks built for different datasets.

One embodiment of the invention may include functional analysis of published conditional gene signature characteristics for phenotypes that are important in breast cancer, such as metastases, survival rate, treatment response, and wound healing. In another embodiment of the invention, published processed gene sets are analyzed to reveal the relationships between the sets as well as the underlying functional categories which unite the genes within a set (common transcription regulation, signaling modules).

As one embodiment of the invention, a new software module or package may be specifically designed for toxicogenomics research. The software module or package may include data analysis workflows and a suggested reporting system for voluntary submission of toxicogenomics data. The software module or package may be integrated with major public toxicogenomics databases and software packages (CEBS, EDGE, Tox-MIAME express and others) as well as complementary software packages and databases.

The software module or package may include the annotated general databases such as protein interactions, drugs, diseases, canonical pathways, etc.; breast cancer specific content (e.g., all published high-throughput datasets, over 1000 annotated genes relevant to breast cancer onsets, and breast cancer pathways maps); data visualization and analysis tools such as networks, pathways, filters; and statistics and the developed data mining tools (e.g., formalized sub-categorization method, identification of bi-modal genes, and pathways-based comparative tools).

The novel data mining process may start with the analysis of toxicogenomics data and elucidation of treatment-specific biological networks. First, protein interaction content from an annotated general databased, e.g., MetaCore™ (GeneGo, Inc.), may be used to generate approximately 15,000 pathway modules representing a "universe" of potential functionality. In the next step microarray data from rats that have undergone three different treatments (e.g., phenobarbital, mestranol and tamoxifen) may be mapped onto these modules. Using Pearson correlation distance and different statistical and clustering procedures, sets of pathways may be identified that have "synchronous" expression pattern among multiple repeats of the same treatment while at the same time showing strong anti-correlation across different treatments.

Taking the breast cancer studies mentioned above, a substantial number of pathways differentiating phenobarbital from mestranol and tamoxifen treatments have been identified while the number of pathways differentiating between tamoxifen and mestranol treatments is more limited. There are no pathways differentiating between treatments with two different concentrations of tamoxifen. Unlike traditional statistical and clustering analysis of the expression on the level of individual genes, the novel process allows reconstruction of connected network modules differentiating between chemical treatments and provides insights into mechanisms of such differences.

A robust categorization of cancers into distinct groups associated with differential treatment response is important for the correct choice of the existing treatments and for the development of selective new drugs for the individual groups, such as imatinib (Glivec), gefitinib (Iressa) and cetuximab (Erbutux), which are effective only if their target is overexpressed or mutated. In the case of metastases, the main utility of gene signatures is to provide a better predictor than current markers for the group of patients with poor prognosis who should receive adjuvant therapy.

The major tools for data analysis are pathways, cellular processes and networks (signaling and metabolic). Pathways are consecutive reaction steps that are either biochemical transformations or sequences of signaling events, such as signal transduction. Functional processes are usually referred to as folders, or categories of proteins needed for execution of distinct cellular functions, such as apoptosis or proteolysis. Unlike pathways, the proteins within categories are not connected by functional links. Both pathways and process categories are static as pre-defined by previous studies, i.e. experimental data can be mapped (via linking data points identifications) on the pathways and processes, but not alter them.

Biological networks are essentially different. They represent combinations of objects (proteins, metabolites, genes etc.) interconnected by links (binary physical protein interactions, single step metabolic reactions, functional correlations etc.) and may be assembled from interaction tables. Biological networks are dynamic, as they are built de novo out of building blocks from binary interactions and are specific for each dataset. The process of data analysis therefore consists of narrowing down the list of potentially many thousands of data points to something more interpretable. This can be achieved by using statistical analysis p-values, different scoring methods for the intersections between categories, and calculation of the relevance of the result to the dataset in question (using the relative saturation of pathways and networks with the data) (FIG. 2).

Networks are by far the most important tool in functional analysis, as they provide the highest resolution (single proteins physically connected), uniquely describe the dataset, and are comprehensive, as the number of connectable proteins on networks substantially exceeds the protein content of all pathways databases and ontologies combined.

Figure 4A:
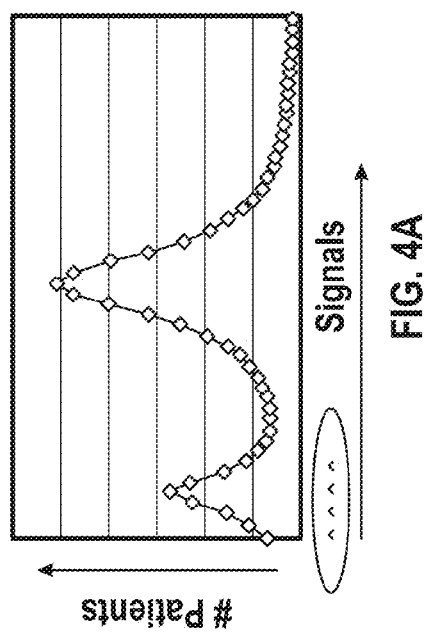
FIG. 4A shows a distribution of signals across the dataset for breast cancer specific bi-modal genes. The four norms are encircled.
Figure 4C:
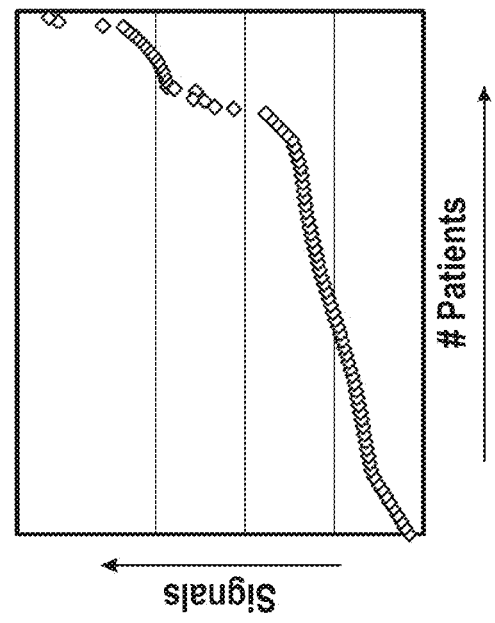
FIG. 4C shows a distribution of GRB7 with the x-axis the patients and the y-axis the expression signals.
Figure 4B:
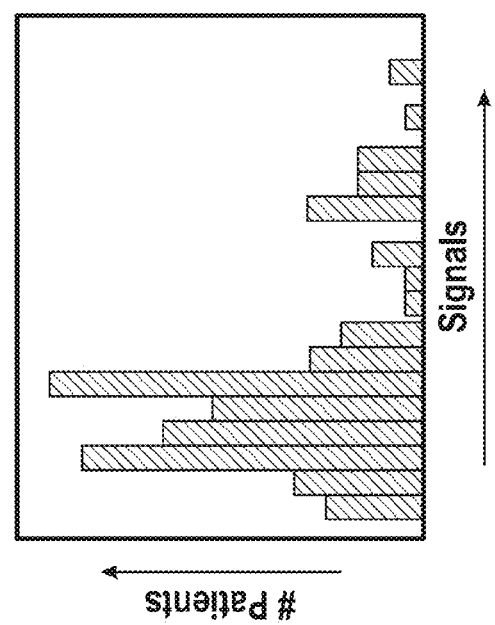
FIG. 4B shows a distribution of GRB7 expression among 122 patients with the x-axis the original expression signals and the y-axis the number of patients with such signals.

Networks were used to evaluate toxicity and human metabolism of acetaminophen (APAP). The structure was processed in MetaDrug™ (GeneGo, Inc., St. Joseph, Mich.) using metabolic cleavage rules and models, and the resultant metabolites were displayed on the networks connected with the metabolizing enzymes. On the same network, microarray gene expression data from livers of the rats intoxicated with high dose of APAP were displayed. FIG. 4A shows a distribution of signals across the dataset for breast cancer specific bi-modal genes. The four norms are encircled. FIG. 4B shows a distribution of GRB7 expression among 122 patients with the x-axis the original expression signals and the y-axis the number of patients with such signals. FIG. 4C shows a distribution of GRB7 with the x-axis the patients and the y-axis the expression signals. The red line marks the threshold which separates the average of signals below threshold (relative 0) $T_i \approx 2.05$. The black line marks $\mu(L_{GRB7}) \approx 0.45$; the green $\mu(U_{GRB7}) \approx 3.65$.

Additional functionality added to the high-throughput data analyzers (i.e., MetaCore™ and MetaDrug™) includes the following items.

Complete assembly of critical mass of human protein interactions in three domains: ligand-receptor interactions; intercellular signaling and core effector (endogenous metabolic reactions, structural protein complexes, interactions on membrane). The interactions from different domains are seamlessly integrated, which enables systems reconstruction of a condition (such as disease, drug response) from large-scale experimental datasets.

Fine mapping of human metabolism is completed, i.e. virtually all published experimentally proven metabolic reactions were assigned to individual enzymes and enzyme-encoding genes. Fine metabolic mapping allowed link signaling with metabolism on merged networks.

The data parsers were expanded to include metabolic data (Chemical Abstract Service (CAS) numbers, smiles, brutto formula), and high-throughput and high content compounds screening data.

Two novel add-on modules were developed for importing and integration of custom interaction data (e.g., co-expression associations in response to a compound, Yeast-2hybrid (Y2H), ChiP/CHIP or pull-down immunoprecipitation data). Custom interactions can be visualized, used as input data for building networks, added to the pathways maps, or permanently installed in the MC/MD database The interactions between mouse and rat genes with no ortholog to human were manually annotated. This is important for detecting the differences between animal model drug expression profiles and human toxicities Integration at the level of data file exchange with several complementary third-party software packages, including Resolver (Rosetta Inpharmatics, Seattle, Wash.), GeneSpring (Agilent Technologies, Santa Clara, Calif.)—suites for management and statistical analysis of microarray expression data; Phylosopher (GeneData, Waltham, Mass.)—a comprehensive bioinformatics suite; Biocrates/ABI software for metabolomics; and Xenobase (University of Michigan Ann Arbor, Mich.)—a translational medicine solution.

One embodiment of the invention has the data mining module or software having both mode of action and off-target effects and toxicity. The methodology consists of scoring the compound response expression data in multiple functional descriptors and categorizing the compound into one or more toxicity categories based on such scoring. This process may be formalized in algorithms and semi-automated.

In another embodiment of the invention, a library of signature networks and other functional descriptors for the analysis of molecular profiles for drug response may be generated. Such descriptors will be built based on functional categories. The applied value of such a library is partly dependent on the quality and scope of toxicogenomics data available for analysis, which is limited to the Chemical Effects on Biological Systems CEBS database (current and future releases, other public databases and peer-review publications). Therefore, a formal process of library generation in a form of workflow wizards may also be generated.

In another embodiment of the invention, workflows and reporting processes may be developed for functional analysis of toxicogenomics data, which will have serious impact on voluntary submission of toxicogenomics data by sponsor companies and their reviewing by federal agencies. Toxicogenomics data submission is not regulated, and, as a result, is submitted in a wide variety of formats using often incompatible experimental environments and analytical procedures. This substantially restricts the use of empirical reference databases such as Iconix's (city state) Drug Matrix™ available for FDA reviewers and increases the probability of misinterpretation of submitted data—which, in turn, increases the risk of approval of potentially toxic compounds to clinical trials and drugs to the market.

Using the invention, data mining and analysis was performed on two datasets published by Sørlie described above. The samples in the 122-patient set represented expression profiles from individual tumors from locally advanced aggressive breast cancers: 115 invasive tumors, four norms and three non-malignant tumors. The set of 295 did not include normal samples. In the original study, 84 samples were divided into five unequal groups by unsupervised hierarchical clustering of the centroid set of 540 genes. The five clusters were called Luminal type A and B, Basal, ERBB2+, normal-like; each featured characteristic sets of over-expressed genes. 38 samples could not be classified in any of five groups. Ten similar cDNA arrays featuring slightly different numbers of genes were used in the study, with >8,000 features each.

The inventive process found that 5797 unique genes on arrays (defined as Locus Link identifications) were common for all 122 samples. The heterogeneity among samples was striking. Not a single gene that was significantly over-expressed statistically in all patients, and only three genes were common between four norms at fold change 2.5. With such little overlap between samples, the straightforward mapping of individual files on the networks was inefficient: every sample featured a unique pathway distribution and poorly comparable networks. The comparative method of signature networks developed earlier is effective for a relatively small number of samples and similar genetic background, and not directly applicable for a set of 122 genome-wide human files, with unknown genetic background.

Figures 7A, 7B:
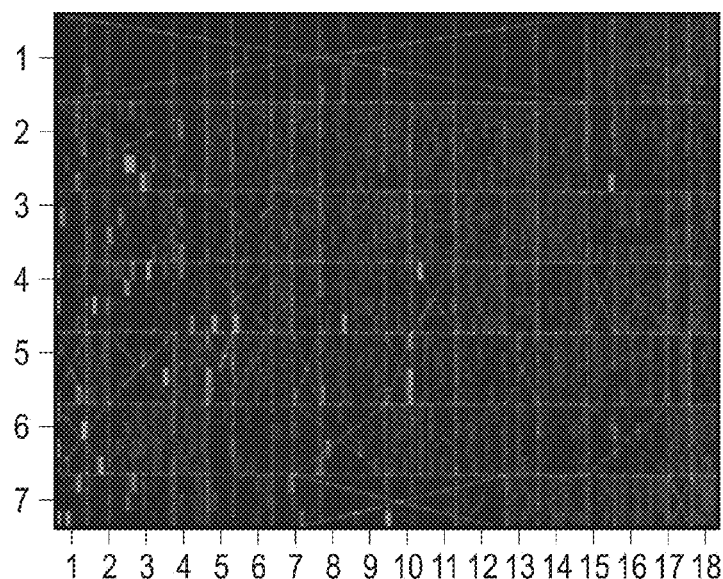
in FIG. 7A, all 122 samples are divided into 18 clusters and in FIG. 7B is a schema of sequential clustering.
Figure 8A:
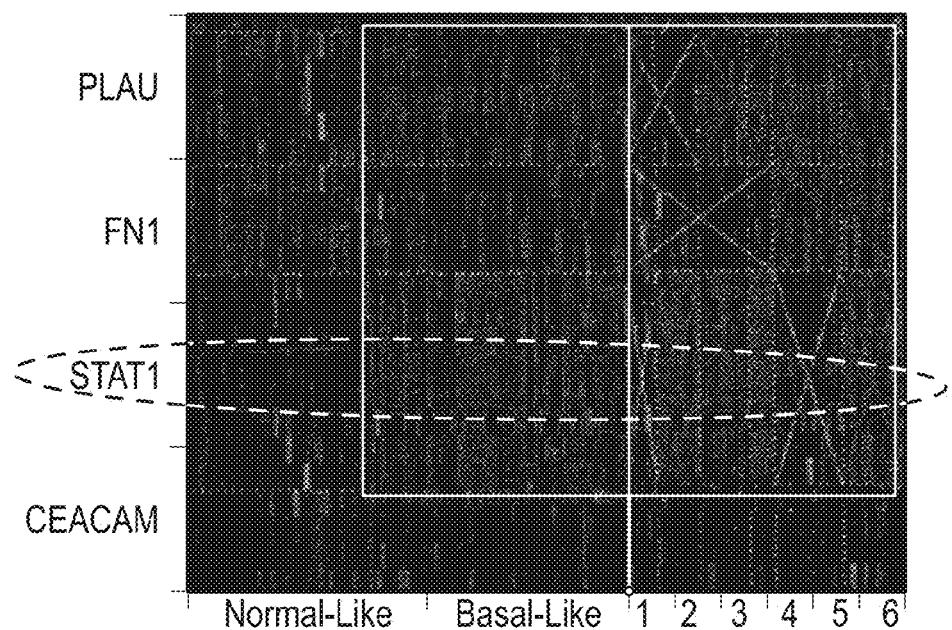
FIG. 8A-C is a representation of the network for STAT1+, P1AU+ and FN1+ groups as input list.
Figure 8B:
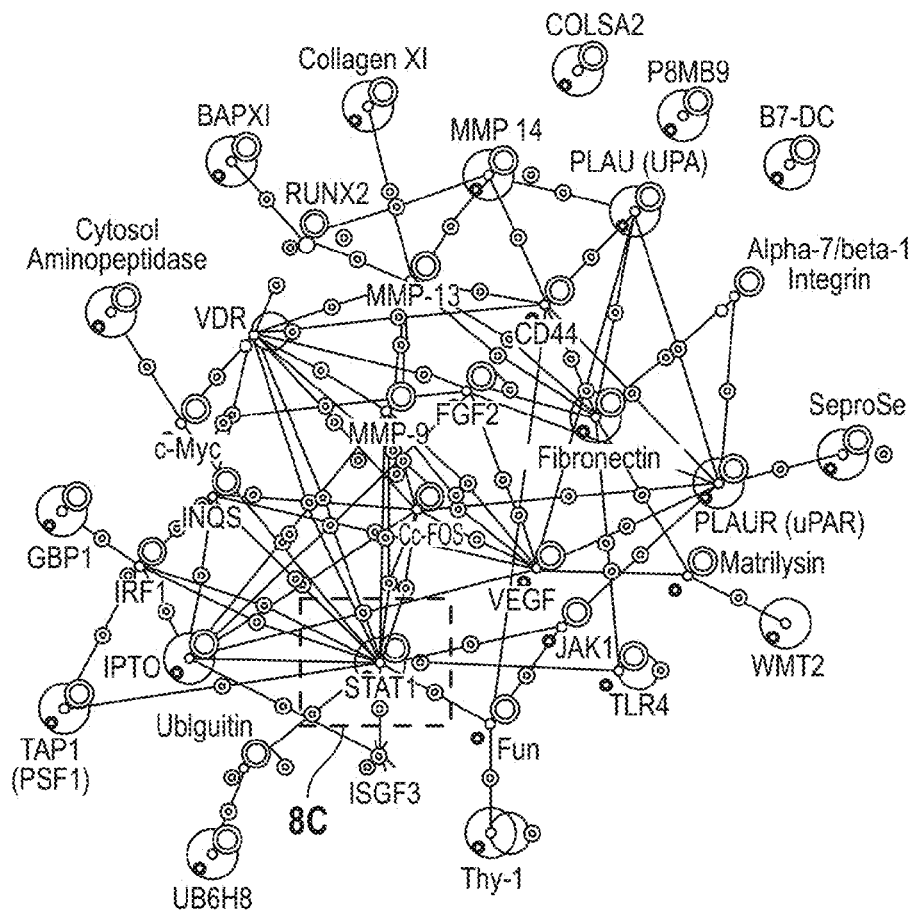
Figure 8C:
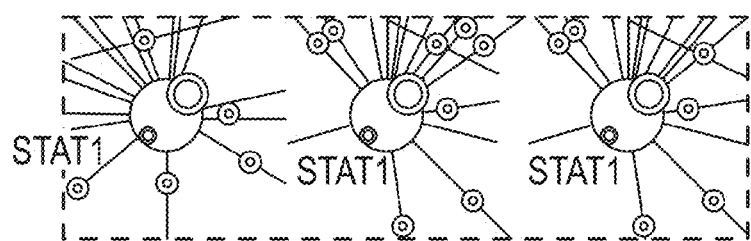

The inventive process also evaluated the functional relevance of Sorlie's clusters in the context of networks and pathways since clustering was carried out by statistical procedures and functional analysis was largely beyond the scope of their studies. The expression patterns in samples within clusters were more synchronous than between randomly chosen samples, but still the intra-cluster variability was high (FIGS. 7 and 8A-C). In FIG. 7, the sequential clustering of the 122 patient set with seven descriptors groups is represented. In FIG. 7A, all 122 samples are divided into 18 clusters and in FIG. 7B is a schema of sequential clustering. FIG. 8A-C is a representation of the network for STAT1+, P1AU+ and FN1+ groups as input list. FIG. 8A is the samples from the basal-like Sorlie cluster mapped on a network. The large number of checkerboard marked genes such as IP10 (encircled in red) should be noted.

Therefore, a clustering approach, rooted in the modern theory of biological networks which states that biological processes are discrete and carried out by relatively small modules of physically inter-connected proteins was used. In order to perform their function properly, the proteins from the same module are likely to be synchronously expressed that may be traced in microarray profiles. In the case of a disease state, such modules may be expressed differently from the norm. Such groups of synchronously expressed groups could be small due to elementary composition and constrains of network topology. Not necessarily highly expressed, these small groups of functionally connected genes are scattered throughout the large-scale arrays and may likely be below the radar screen of clustering methods. If such synchronously expressed modules could be identified, then characteristic signature networks could be built which would be characteristic for samples clusters and likely correlated with biological and clinical phenotypes. The general workflow of clustering is present in FIG. 2.

The original study team used ten similar but still different arrays, and a number of genes common between all samples were array-dependent. For each common gene, the correlation coefficient for array-dependency has been calculated which relates the difference between means for each array and the dispersion between arrays with a correction for the group (array) size, and the maximum for each group is chosen. i—gene number on array; r; $k_1$ and $k_2$—type of array/gene pool; $j_k$—sample's number on array of k type; $\#j_k$—the number of samples on the arrays of k type; $s_i^{j_k}$—a signal of gene i in the sample $j_k$; $\mu(s_i^{j_k})$—mean between signals of gene i on the arrays of k type; $\sigma(s_i^{j_k})$—standard deviation for the signals of gene i in the samples from arrays of k type.

$$\rho_i = \max_{k_1 \neq k_2} \frac{\left(\mu\left(s_i^{j_{k_1}}\right) - \mu\left(s_i^{j_{k_2}}\right)\right)^2}{\sigma\left(s_i^{j_{k_1}}\right)^2 + \sigma\left(s_i^{j_{k_2}}\right)^2} \frac{1}{\frac{1}{\#j_{k_1}} + \frac{1}{\#j_{k_2}}}$$

As $p_i$ increases, correlation with an array increases. Genes with $p_i > 15$ are highly array dependent; this excluded 869 array dependent genes in the initial analysis.

In the next step, the distribution of expression values was compared throughout the whole set of 122 samples for each gene and it was noticed that the expression of some genes tend to cluster into two levels—or modes. In other words, the expression function seems to be rather discrete with two peaks, rather than continuous. We calculated such bi-modality for each gene in both the 122 and 295 patient sets. The following are parameters used in the analysis.

For each gene, a relative threshold expression value was chosen, and the signals from all samples were split onto $L_i$ (lower than threshold values) and $U_i$ (higher than threshold values) groups For each gene, the mean was calculated for the L group $$\mu(L_i) = \mu^j(s_i^j)_{j \in L_i},$$

the mean for the U group $$\mu(U_i) = \mu^j(s_i^j)_{j \in U_i},$$

and the sum of squares of differences between individual genes signals and means in both groups $$\gamma(L_i, U_i) = \sum_{j \in L_i} (s_i^j - \mu(L_i))^2 + \sum_{j \in U_i} (s_i^j - \mu(U_i))^2,$$

where i—the gene number; $j \in L_i$—the samples' numbers in which signals for gene i are placed into $L_i$; $j \in U_i$—the samples' numbers in which signals for gene i are placed into $U_i$; $s_i^j$—a signal of gene i in the sample j.

The threshold for each gene was chosen based on minimization of $\gamma(L_i, U_i)$ The resulted partition has a property of threshold to be equal to half of the sum of the means for L and U groups.

$$T_i = \frac{\mu(L_i) + \mu(U_i)}{2}, s_i^{j \in L_i} < T_i \text{ and } s_i^{j \in U_i} > T_i,$$

Next, for each gene the bi-modality coefficient was calculated.

$$\tau_i = \frac{\mu(U_i) - \mu(L_i)}{\sqrt{\frac{\gamma(L_i, U_i)}{\#L_i + \#U_i}}}$$

where $\#L_i$—the number of signals in $L_i$ group, $\#U_i$—the number of signals in $U_i$ group. A gene is considered bi-modal if $\tau_i > 2.596$. There were 1976 such genes; roughly 40% of the array-independent genes. A typical bi-modal gene, GRB7, has $\tau_{GRB7} = 4.762$ and the following distribution between samples (FIG. 4).

The expression values in the four normal samples were clustered in one peak (mode) close to each other—a highly non-random event (FIG. 4A). In such cases, bi-modality is conditional (associated with breast cancer) and the disease expression mode is distinctly different than normal. Bi-modal disease-specific genes could be highly important for understanding the disease mechanism, and as the source of biomarkers and drug targets. The pool of breast cancer-specific bi-modal genes was extracted as following:

The mean for normal patients was calculated $$\mu_i^N = \mu(s_i^{j \in N}),$$

where N=samples from normal patients
In the case of $$\mu_i^N < T_i,$$

the gene expression values were transformed by $$\bar{s}_i^j = \frac{s_i^j - \mu(L_i)}{\mu(U_i) - \mu(L_i)};$$

otherwise $$\bar{s}_i^j = \frac{s_i^j - \mu(U_i)}{\mu(L_i) - \mu(U_i)}.$$

Therefore, $$\bar{\mu}_i^N = \mu(\bar{s}_i^{j \in N}) \le \frac{1}{2},$$

$$\bar{\mu}(\bar{L}_i) = \mu^j(\bar{s}_i^j)_{j \in L_i} = 0,$$

$$\bar{\mu}(\bar{U}_i) = \mu^j(\bar{s}_i^j)_{j \in U_i} = 1,$$

$$T_i = \frac{\bar{\mu}(\bar{L}_i) + \bar{\mu}(\bar{U}_i)}{2} = \frac{1}{2}.$$

For each gene, the standard deviation was calculated for transformed values in normal samples $$\bar{\sigma}_i^N = \sigma(\bar{s}_i^{j \in N}).$$

A gene was considered as breast cancer-dependent bi-modal if it qualified as bi-modal by bi-modality coefficient $\tau_i > 2.596$ and if $$\bar{\mu}_i^N = \mu(\bar{s}_i^{j \in N}) < \frac{1}{3}$$

and $$\bar{\sigma}_i^N = \sigma(\bar{s}_i^{j \in N}) < \frac{1}{3}.$$

Overall, 949 bi-modal breast cancer dependent genes were identified.

Figure 5B:
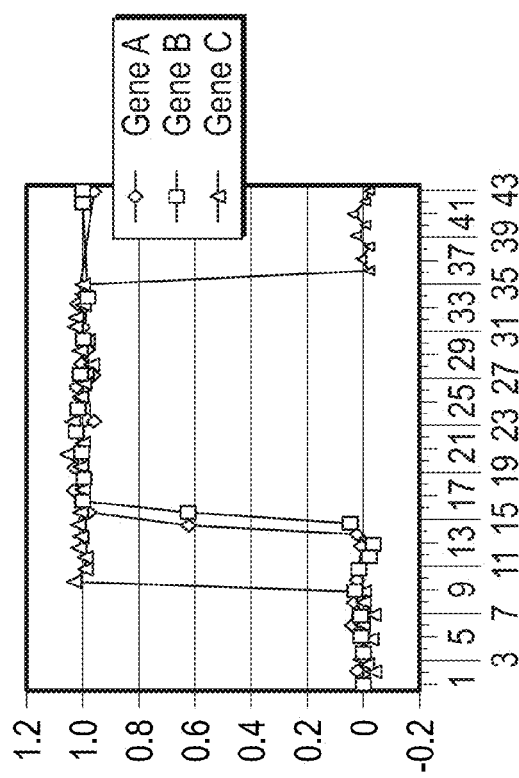
FIG. 5 is a representation of the transformation of expression signals according to bi-modality, after normalization of the original signals as shown in FIG. 5A the signals look as shown on FIG. 5B. In principle, such transformation is applicable for any gene expression distribution. The 122 samples are shown in the original and transformed signals scale on FIGS. 5C and 5D, correspondingly.
Figure 5D:
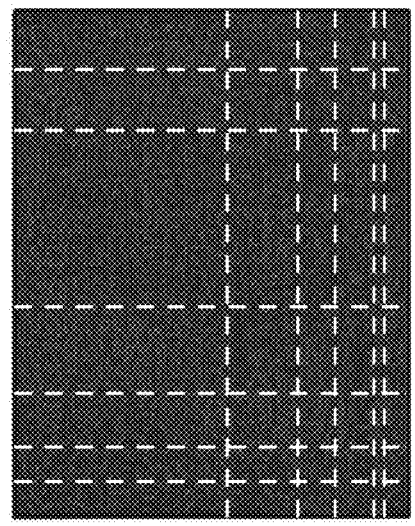
Figure 5A:
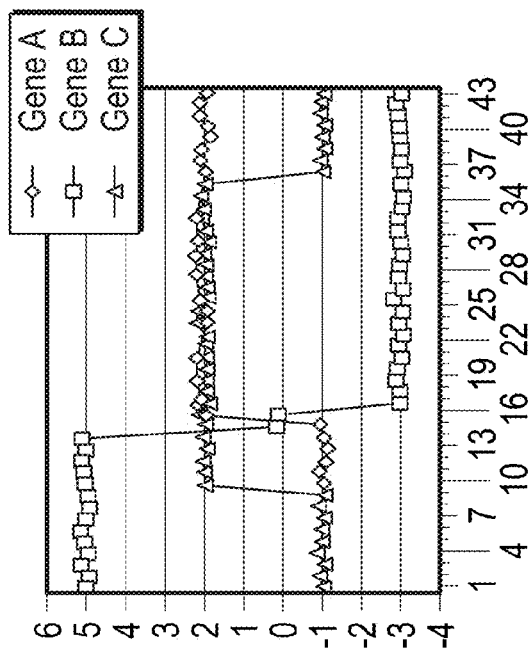
Figure 5C:
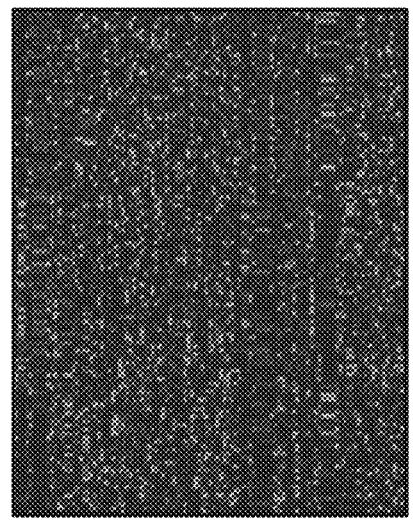

Next, the signals were normalized by bi-modality transformation in order to clearly separate the patient samples with signals in the normal peak from the disease peak. The peak around norm was designated as 0 and the other peak as 1. This normalization is needed in order to minimize the distance between the genes that separate patients in the same way. This minimization is important. Considering a hypothetical case of three bimodal genes (FIGS. 4A and 4B), experiments are on OX; original signals on OY. The distances between genes A and C, will be much smaller than between A and B. The distance can be defined as the sum of differences between signals in all patients. A-C distance here is 40; A-B distance >200. However, if the signals are transformed, then genes A and B divide patients in the same way, but C behaves very differently. After normalization of the original signals as shown in FIG. 5A the signals look as shown on FIG. 5B. In principle, such transformation is applicable for any gene expression distribution. The 122 samples are shown in the original and transformed signals scale on FIGS. 5C and 5D, correspondingly.

As mentioned above, approximately 1,000 genes have been shown to be relevant to breast cancer in the literature (with particular SNPs, mutations, genome rearrangements, gene amplifications and promoter methylation; splice variants, RNA and protein abundance associated with certain onsets of the disease). Among those, 56 genes were reported as breast cancer genetic markers; 35 of these genes were spotted on the array. Fifteen of these 35 appeared to be breast cancer dependent bimodal. One of the fifteen was ERBB2 from the known amplicon linked to breast cancer.

dom set of 29 genes to contain eighteen bimodal genes out of a random such event happen random is 4.5e-7. The genes within the groups were closely functionally connected, and could be assembled into small networks.

TABLE 2

29 Gene Descriptor Sets for Sub-Categorization of Breast Cancer Patients from 122 Patient Dataset

| Group 1 | Group 2 | Group 3 | Group 4 | Group 5 | Group 6 | Group 7 |
| --- | --- | --- | --- | --- | --- | --- |
| (ERBB2) | (ESR1) | (KRT5) | (KRT8/18) | (PLAU) | (FN1) | (CEACAM) |
| ERBB2 | ESR1 | KRT5 | KRT18 | PLAU | STAT1 | CEACAM5 |
| STAED3 | GATA3 | KRT17 | KRT8 | COL5A2 | UBE2L6 | CEACAM6 |
| GRB7 | XBP1 | TRIM29 | PPP2CA | FAP | TAP1 | CEACAM7 |
| THRAP4 | TFF3 | GABRP | KRT8L2 | THY1 | LAP3 | |
| PPARBP | ACADSB | | | | | |

Figure 6A:
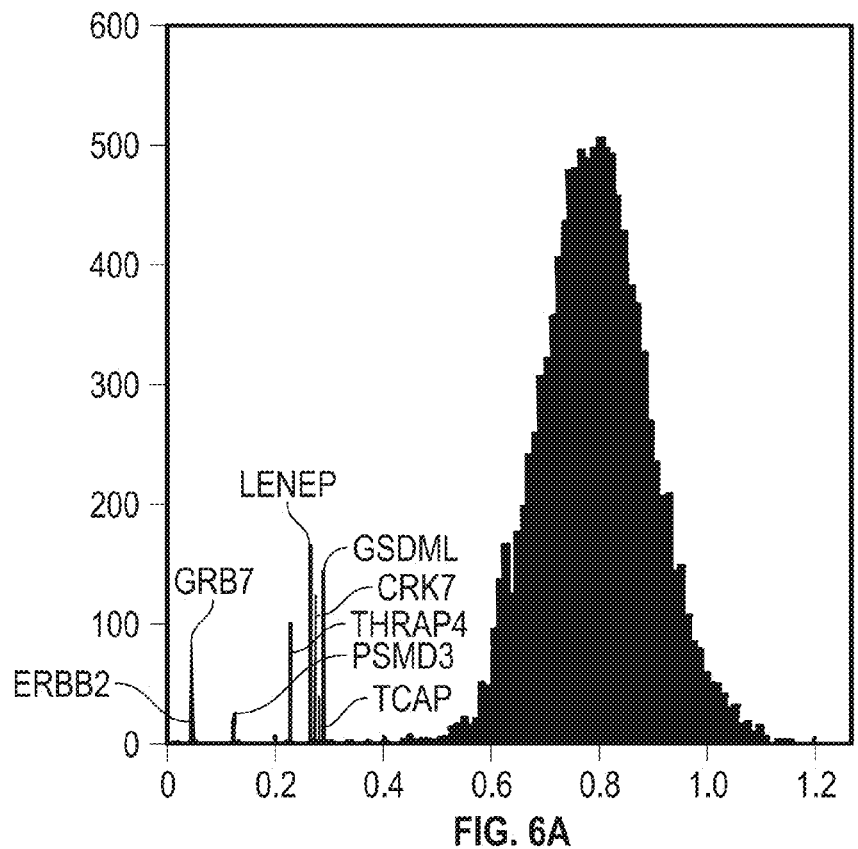
FIG. 6A-C is a representation of the identification of the close groups of genes in the space of 122 samples.
Figure 6B:
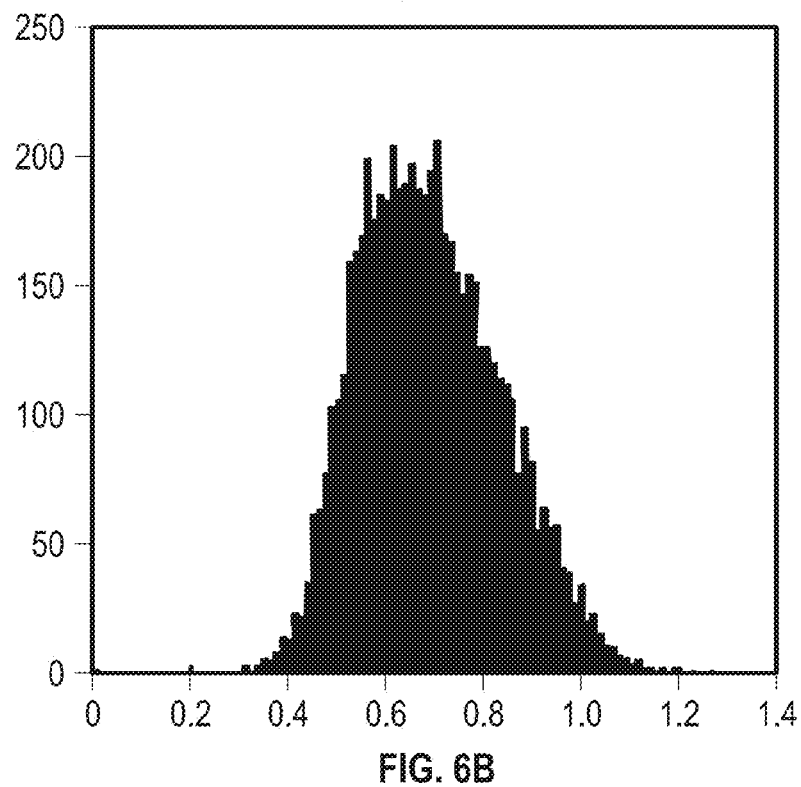
Figure 6C:
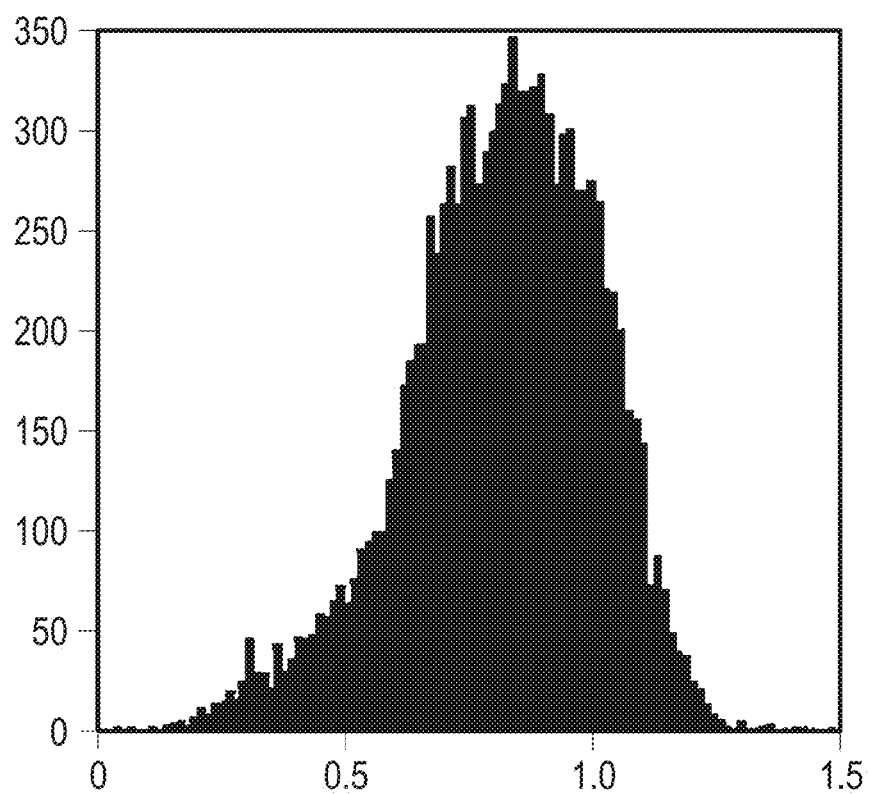

As the next step of the analysis, the close neighbors groups for each of these 35 genes was calculated; close neighbors are defined as the genes with the most similar expression behavior. The groups may be characterized by two parameters: 1) the genes within a group are close to each other in signal distribution vector among 122 (or 295) patients and 2) the genes within a group are situated close to each other in distribution (FIG. 6A-C). For each such gene, we calculated the distances between its vector and vectors for all other genes among 122 patients;

$$\rho_{i_1, i_2} = 1 - \frac{\sum_j \overline{s}_{i_1}^j \overline{s}_{i_2}^j}{\sqrt{\sum_j \overline{s}_{i_1}^{j2} \sum_j \overline{s}_{i_2}^{j2}}}.$$

$i_0$=gene index among 122 patients
j=sample number
$\overline{s}_i^j$=signal of gene i in the sample j after transformation.

The distances between genes varied between 0 and 2. The genes were considered close in transformed values if the p value was small (0.0-0.4), and there were few genes with similar p values relatively to the main distribution, such as the case of GRB7 group (FIG. 6A). Two other cases are shown in FIGS. 6B and 6C. In case of HMGA1, no close group can be identified. The closest gene to HMGA1 is at the distance of 0.3 and the main distribution is close to this gene. The distance from the closest gene to query is small (<0.05), a dozen other genes are within 0.2, and determination of the closest group is uncertain. In FIG. 6A-C, OX is the relative distances from the query gene to all 4928 array-independent genes and OY is the number of genes. FIG. 6A shows a clear close group around ERBB2/GRB7 (encircled); FIG. 6B shows no close group for HMGA1 as query gene; and FIG. 6C shows a vague group for JAG2 (encircled).

Nine genes from the list of 35 fetched the groups of synchronously expressed genes. Surprisingly, all nine were from the set of fifteen breast cancer specific bi-modals and none from 21 non-bimodals. Four of the nine genes appeared to be in the same groups. Including the nine query genes, 29 genes were identified and split into 7 groups (Table 2). Importantly, eighteen of 29 genes were breast cancer dependent bimodal genes.

The synchronous expression in groups is shown in FIG. 5. This is a highly non-random event. The probability of a ran- Each of the seven groups of close neighbor genes divides 122 samples into + and − clusters depending on whether their transformed expression values are closer to 0 or 1, with a threshold 0.5. This procedure may be applied sequentially, starting with the group with the highest τ(L,U). In the datasets of 122, ERBB2 and ESR1 groups have the highest τ(L,U) value, and clustering can be started with either group. The ESR group splits the dataset into ESR+ and ESR− clusters; they are divided into four clusters by ERBB2: ERBB+/ESR+; ERBB−/ESR+; ERBB−/ESR+; ERBB−/ESR− and so on. At every step, the parameters of bi-modality are recalculated for every cluster. The division stops when there are fewer than 5 patients left in the group or when no bimodal genes are left in the cluster.

Eventually, the whole set will be split into clusters characterized by the unique status of each of seven descriptor groups (FIG. 6A-C). For example, any sample in cluster 8 could be characterized as a string: ERBB2+/ESR1+/KRT5+/CEACAM−/STAT1−/PLAU−. The entire 2D map can be considered as a matrix of eighteen clusters multiplied by seven groups.

Not every group decisively separates every cluster at each step. For instance, the expression status of group 5 (PLAU) cannot separate clusters 12 and 13, but is key in dividing clusters 8 and 9. Therefore, the string of consecutive bilateral parsing defines each cluster uniquely and distinguishes it from other clusters. Two features of such sequential clustering are important for using this method for diagnostics. First, virtually all samples were parsed into one or another cluster, compared to one-third unclassified samples from Sørlie's clustering. Second, the sample in the clusters form concise networks and consistently map to the pathways due to synchronous expression within groups (FIG. 7). Sequential clustering can be performed in a different order, for example starting with ESR1. In such case, we may end up with fifteen clusters, which are closely related to these eighteen. In order to evaluate the method on an independent set, the same seven groups were used on a set of 295 patients carried out on a similar but different cDNA array. All 295 samples were divided into the same 18 clusters using the same sequential clustering schema. Two additional groups (64 genes) were extracted from the set of 295 (as expected for the larger set).

The clusters determined in this study are biologically meaningful, which can be seen by mapping of the cluster data on pathways and networks, e.g., the 295 patient dataset from Sørlie. First, the original clusters of Sørlie are transformed into signals and applied to the nine groups determined in the study for mapping. The selected groups of patients which belonged to basal-like cluster, were used as an input list for building networks. Most basal-like samples were characterized by over-expression of STAT1, PLAU and FN1 groups. However, for some samples within the cluster, these groups are down-regulated. In the case of our schema, our clusters 1-6 are also characterized by the same PLAU– FN– STAT1 groups, but the division is more clear, for instance we clearly separate on FN1+ (clusters 1-4) and FN1– (clusters 5,6).

Figure 9B:
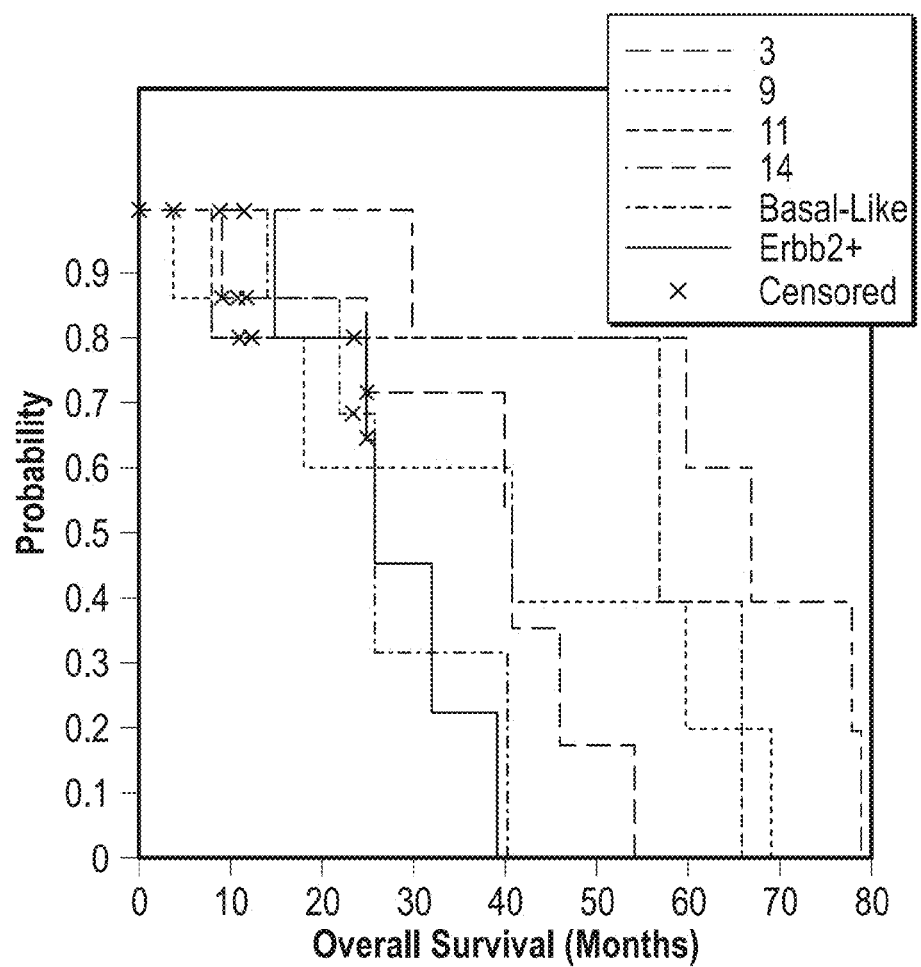
Figure 10:
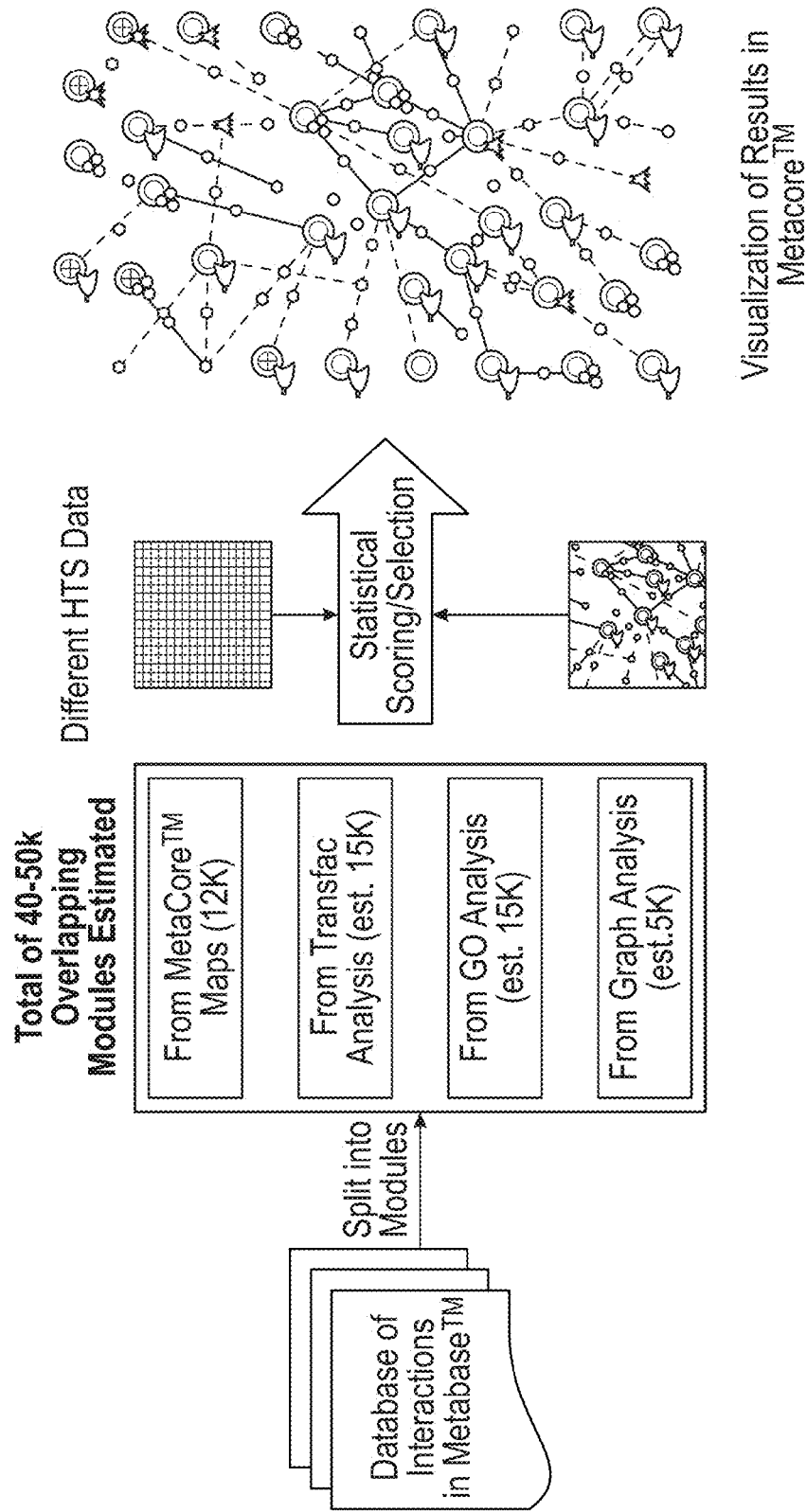
FIG. 10 is a representation of the reconstruction of conditional sub-networks from pathways.

Another example is presented in FIG. 9A-B. The complete sample content of cluster 9 from this study set of 295 patients was mapped on MetaCore™'s pathway maps as shown in FIG. 9A. The expression for GRB7, ERBB4 and ERBB2 are consistently down-regulated in all samples of the cluster. All members of cluster 9 correspond to the Luminal B cluster defined by Chang et al. in the same 295 patient dataset. All the samples from the Luminal B cluster are mapped on the same pathway maps (FIG. 9A). In this case, expression profiles for ERBB2, GRB7 and ERBB4 are inconsistent throughout the samples: some of the genes are down-regulated, and some others are up-regulated.

The average survival rate for 72 patients with locally advanced cancers was also evaluated; the same patients tested by Sørlie in the original study were used. Only the clusters with >5 patient samples are included. The test shows that average survival time varies significantly from 40 months for cluster 9 to 80 months for cluster 14 (FIG. 9B).

Figure 15:
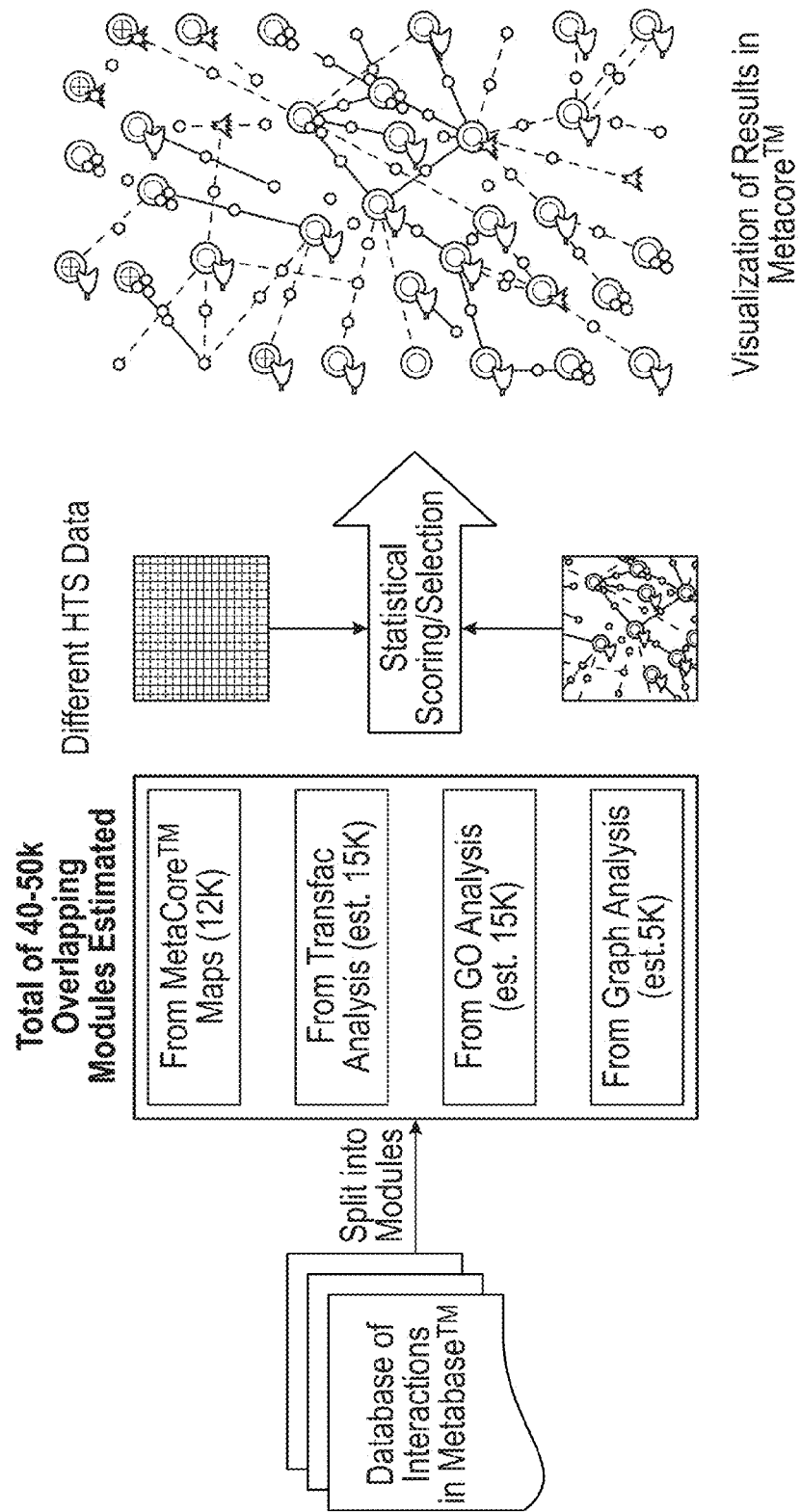
FIG. 15 is a representation of the reconstruction of conditional sub-networks from pathways.

As described above, a method to develop signature methods is a novel method for reconstruction of condition-specific networks for genetically homogeneous data sets, such as toxicogenomics gene expression data from animal models and cell cultures. The approach consists of computation and comparison of sub-graphs (modules) that are most differentially affected by drug action using a combination of biological and topological criteria. Conditional molecular data (drug-specific gene expression) is then mapped onto these sub-graphs and statistically scored (FIG. 15).

The signature networks method has been used on data from several toxicogenomics experiments in response to drug treatments in rats in collaboration with the FDA. This dataset contains microarray gene expression from the livers of rats exposed to three drugs: phenobarbital, mestranol, and tamoxifen. The data were produced by custom cDNA two-channel arrays. Five biological repeats were performed for each treatment and a set of five samples from the untreated animals were analyzed. Biological modularity suggests that cellular functions are performed by groups of proteins that temporarily work in concert. The interaction space between proteins within the module is statistically enriched compared to inter-module interactions, and therefore modules can be computed and visualized as sub-graphs on the larger networks.

A pre-computed comprehensive set of overlapping canonical pathways derived from 450 signaling and metabolic pathway maps manually created using a general database, MetaCore™ was obtained. These pathways then were used as a framework for mapping experimental datasets as well as to calculate the network modules most relevant to specific pathways (FIG. 15). The maps feature approximately 3,000 proteins and over 2,000 overlapping human pathways. On these maps, typical signaling inputs (indicated by block arrows) are identified. The network modules were then generated as chains of interactions/reactions initiated at one of the signaling inputs and followed down to the last protein identified in the canonical pathway; such termini often are transcription factors and their targets. These pathways represent linear modules of cell signaling, usually parts of signaling cascades between secondary messengers and transcription factors. Due to branching (variability between the overlapping pathways) in many signaling cascades, the total number of such chains was quite large—about 12,000. We have limited this number by selecting the pathways present on at least two different maps. The 2,200 conserved pathway fragments were pre-assembled and stored in a file with the following format:

Pathway ID: Network ID1→Network ID2→Network ID3→ . . .

Figure 11:
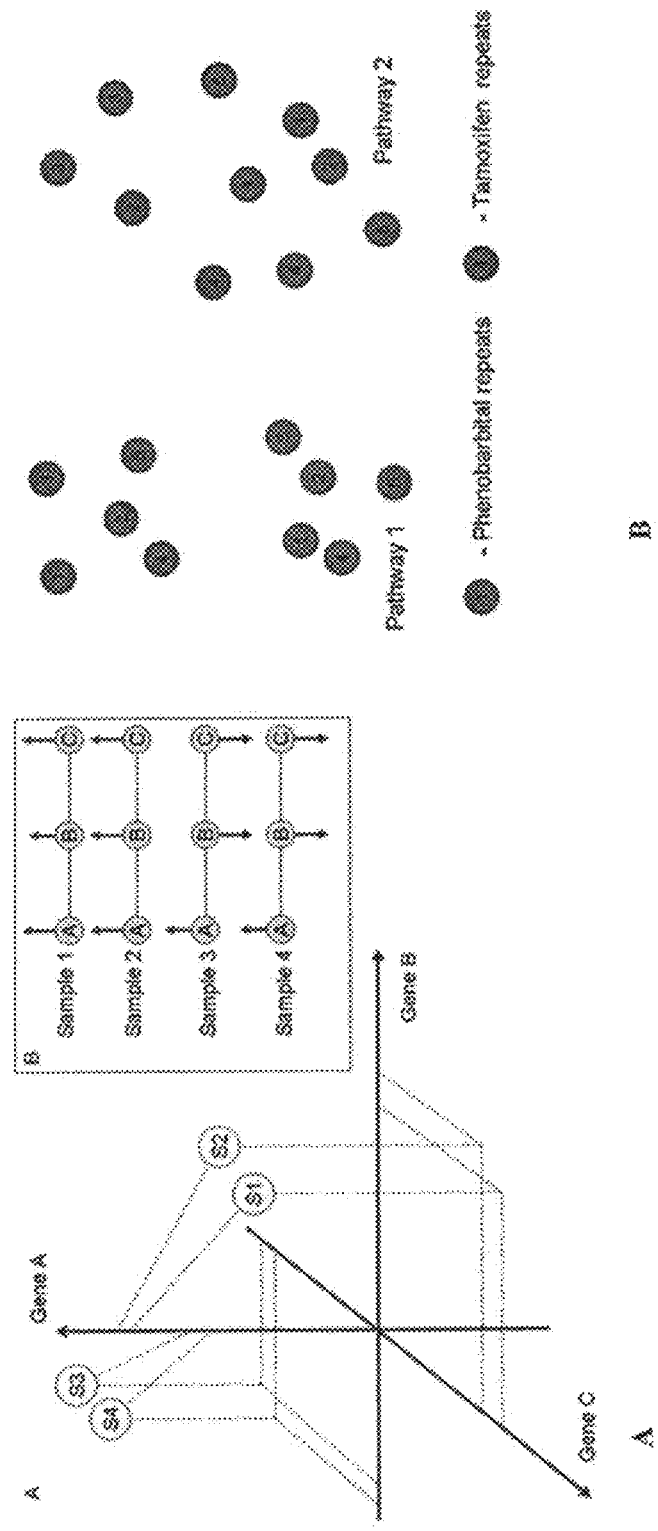
FIG. 11 is a representation of the calculation of distances between samples in the pathway's gene expression space.

The network identifications were disassembled into the lists of corresponding gene identifications and the files were parsed into the general database as gene lists. Next, we calculated relative distances between samples in the space of gene expression of individual pathways. The idea is illustrated in FIGS. 11 and 12. A pathway with three genes is used as an example (representation of a larger pathway would require a projection of multi-dimensional space). Samples are represented by points (vectors) in this space according to their expression values. After all the data was imported, we used a metric to compute the distances between samples in each pathway. For example, if we had a pathway defined as:

Pathway 1: [gene 1, gene 2, gene 3, gene 4]

and each gene had data associated with it from the gene expression dataset,

|        | Sample 1 | Sample 2 | Sample 3 | Sample 4 |
|--------|----------|----------|----------|----------|
| Gene 1 | 1        | 4        | 3        | 2        |
| Gene 2 | 4        | 2        | 7        | 6        |
| Gene 3 | 2        | 9        | 3        | 8        |
| Gene 4 | 2        | 5        | 4        | 2        | the distances were computed for all combinations of samples $$\binom{n}{k},$$

where k=2 and n=the total=the total number of samples. This means the order in sample pairs is not important (i.e. sample 1/sample 4 are the same as sample 4/sample 1.) The possible pathways combinations: Sample 1/Sample 2; Sample 1/Sample 3; Sample 1/Sample 4; Sample 2/Sample 3; Sample 2/Sample 4; Sample 3/Sample 4. Only the distances between the unique samples are considered, as the distance function is symmetric: the distance between sample 1 and sample 3 is the same as between sample 3 and sample 1. Euclidean and Pearson distance functions were utilized for calculating the distances between samples.

Euclidean Distance:

$$d_{x,y} = \frac{1}{n}\sum_{i=1}^{n}(x_i y_i)^2$$

$d_{x,y}$—distance between sample x and sample y
n—the number of genes in the pathway
i—gene
$x_i$—expression value for gene i in sample x
$y_i$—expression value for gene i in sample y Pearson Distance:

$$r_{x,y} = \frac{1}{n}\sum_{i=1}^{n}\left(\frac{x_i - \overline{x}}{\sigma_x}\right)\left(\frac{y_i - \overline{y}}{\sigma_y}\right)$$

$$d_{x,y} = 1 - r_{x,y}$$

$d_{x,y}$—distance between sample x and sample y
$r_{x,y}$—correlation coefficient for sample x/sample y
n—number of genes in the pathway
i—gene $x_i$—expression value for gene i in sample x
$y_i$—expression value for gene i in sample y
$\bar{x}$—mean expression for sample x
$\bar{y}$—mean expression for sample y
$\sigma_x$—standard deviation of expression values in sample x
$\sigma_y$—standard deviation of expression values in sample x For every distance function, we have computed the distances between samples for all pathways:

|  | S1/S2 | S1/S3 | S1/S4 | S2/S3 | S2/S4 | S3/S4 |
|---|---|---|---|---|---|---|
| Pathway 1 |  |  |  |  |  |  |
| ... |  |  |  |  |  |  |
| Pathway n |  |  |  |  |  |  |

FIG. 11A is a representation of the calculation of distances between samples in the pathway's gene expression space. A hypothetical pathway is shown, consisting of three proteins A, B and C. Samples are represented as points in 3-dimensional space of gene expression. Note grouping of samples. Also pathways corresponding to gene expression (fold change compared to control) are represented by arrows. FIG. 11B is a representation of clustering of samples in the pathway's gene expression space. For Pathway 1 the distance between the samples corresponding to the same treatment is statistically smaller than inter-treatment distance. For Pathway 2 no such distinction could be made.

Figure 12A:
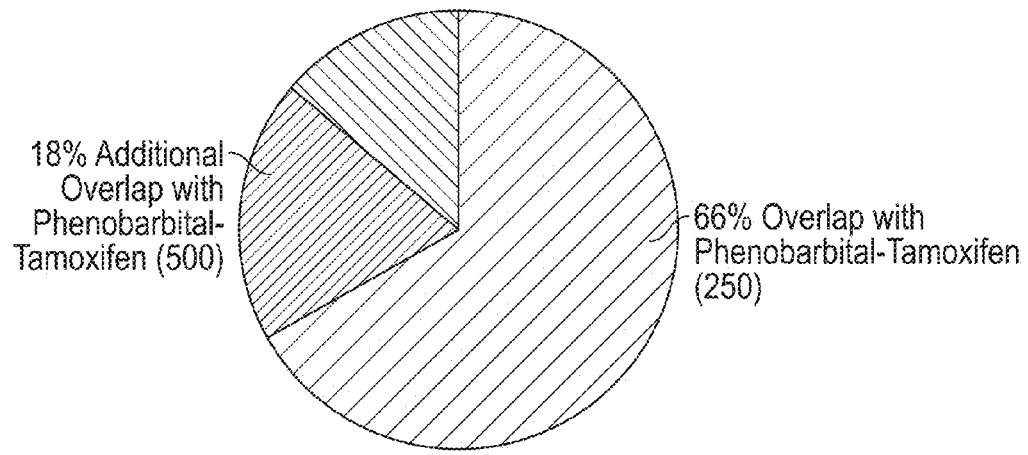
FIG. 12A-B is a representation of the characterization of the overlap between groups of genes identified as differentiating between treatment conditions.
Figure 12B:
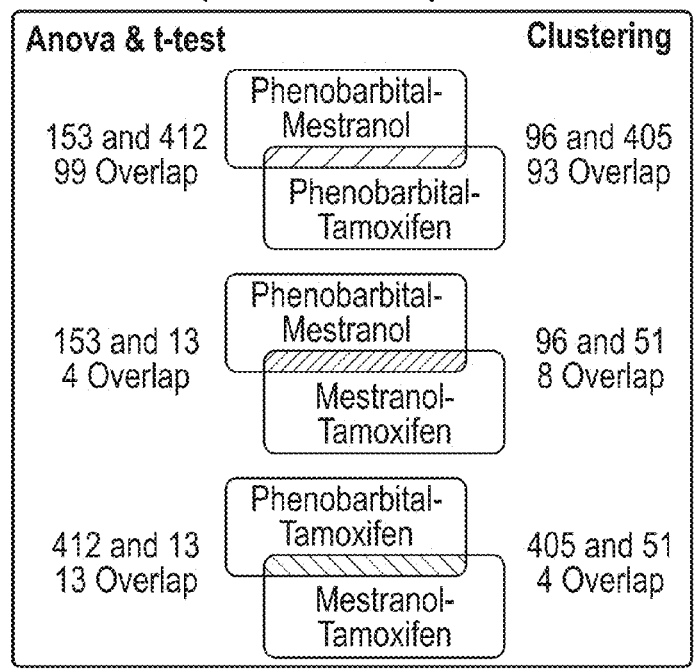

FIG. 12A-B is a representation of the characterization of the overlap between groups of genes identified as differentiating between treatment conditions. In (A), the overlap between the genes differentiating between the phenobarbital-mestranol and phenobarbital-tamoxifen treatments is shown. About 66% of the total number of genes that differentiate between phenobarbital-mestranol also differentiate between Phenobarbital-tamoxifen and about 18% represents the genes that differentiate between phenobarbital and higher concentration of tamoxifen, but do not differentiate between the phenobarbital and lower concentrations of tamoxifen. In (B), the overlap between the groups of genes differentiating between all treatment pairs is represented.

This procedure results in a matrix of distances between samples in the space of gene expression pattern of individual pathway modules. The distances can be grouped according to arbitrarily defined types of samples. The distances were compared between repeat samples for the same treatment versus samples from different treatments. For every pathway, the statistical hypothesis that the average distance between repeats of the same treatment is significantly different than the average distance between different treatments was tested. If the hypothesis is confirmed for a pathway, calculations are performed to determine which particular pair of treatments the repeat samples for the same treatment cluster together, while inter-treatment distances are larger (FIG. 11). The criterion for success was identification of distinctive pathways or groups of pathways that distinguish between treatment responses, e.g. mestranol from phenobarbital. The selected pathways were grouped into clusters based on the statistical t-test. In the next step, clusters that clearly distinguish between two treatments are selected. For instance, the pathways that distinguish mestranol from tamoxifen treatment had to satisfy the condition that both distances between mestranol repeats and distances between phenobarbital repeats are statistically smaller than mestranol to phenobarbital distance. Upon selecting the groups, the genes from the pathways distinguishing between two particular treatments were imported into the MetaCore™ general database for further analysis.

Based on the analysis described above, it was found that:
Phenobarbital vs. tamoxifen: 163 pathways containing a total of 131 unique genes;
Mestranol vs. tamoxifen: 3 pathways containing a total of 15 genes; and
Mestranol vs. phenobarbital: 54 pathways containing a total of 151 genes.

No pathways were found that distinguished between responses to different tamoxifen concentrations. Another important observation is the number of pathways that distinguish mestranol from tamoxifen was substantially smaller than those distinguishing phenobarbital from both mestranol and tamoxifen treatments. No pathways were found that distinguish between responses to different tamoxifen concentrations. Mestranol and tamoxifen have similar structures and biological targets (both are ligands for estrogen receptor); phenobarbital is distinct from this pair structurally as well as by mode of action. (See Table 3 for the statistical analysis summary.)

TABLE 3 t-Test versus Clustering Analysis

| Treatments | Number of pathways identified by t-Test | Number of pathways identified by clustering | Genes identified by t-Test | Genes identified by clustering | Overlap and the significance of the overlap (p-value) |
|---|---|---|---|---|---|
| Phenobarbital vs. Mestranol | 112 | 62 | 153 | 96 | 84 (p = $10^{-47}$) |
| Phenobarbital vs. Tamoxifen (250 nM) | 258 | 154 | 293 | 271 | 225 (p = $10^{-60}$) |
| Phenobarbital vs. Tamoxifen (500 nM) | 431 | 353 | 373 | 359 | 339 (p = $10^{-106}$) |

TABLE 3-continued t-Test versus Clustering Analysis

| Treatments | Number of pathways identified by t-Test | Number of pathways identified by clustering | Genes identified by t-Test | Genes identified by clustering | Overlap and the significance of the overlap (p-value) |
|---|---|---|---|---|---|
| Mestranol vs. Tamoxifen (250 nM) | 4 | 6 | 9 | 47 | 1 (p = 0.5) |
| Mestranol vs. Tamoxifen (500 nM) | 1 | 1 | 4 | 4 | 4 (p = $10^{-10}$) |
| Tamoxifen (250 nM) vs. Tamoxifen (500 nM) | 0 | 0 | 0 | 0 | 0 |

Next, the lists of genes from generated groups (the unions of genes in differential pathways) were imported into the current version of the general database to explore network connectivity. The "Direct Interactions" network building algorithm was applied. This algorithm retrieves all the interactions connecting genes of interest to each other (FIG. 16A). The networks were overlaid with expression data that had been converted into log-ratios of gene expression levels between treated and untreated animals. The up-regulated genes are marked with red circles, the down-regulated ones with blue circles. The networks contained a substantial number of genes that are negatively correlated between treatments. Interestingly, the fold change values for most of these genes are relatively low, i.e. within 10% to 30%.

However these genes assemble into an interconnected network with synchronous differential response to treatments. The drug response networks produced by this method can be characterized by different parameters. For instance, their genes/proteins content can be parsed onto such functional categories as canonical pathway maps, GO processes, pre-set process networks (e.g., GeneGo St. Joseph, Mich. processes), as well as categories for diseases and toxicities. Smaller sub-graphs of signature networks for the genes related to individual processes (for instance, a mitosis sub-graph, FIG. 16B) could be also considered as a functional descriptor between conditions. The p-value distribution of functional categories can be considered as the network parameters, and the functional distance between networks can be evaluated based on the number of matching functional categories and more subtle derivative parameters. According to these distributions, the networks are essentially different, although one of the original datasets used for generating the networks is the same (phenobarbital expression profile).

Two important advantages of the network comparison method compared to conventional statistical procedures should be noted. These are illustrated in FIG. 16C, which displays the highest scored pathway map, CREB pathway, for gene content of tamoxifen/phenobarbital network. The expression data for phenobarbital and tamoxifen files were mapped and displayed as red (up-regulation based on fold change) and blue (down-regulation based on fold change) histograms. No threshold was set up for fold change and P-values. The mapping demonstrates an amazing consistency between data points within individual datasets on the pathways. Almost all phenobarbital genes are up-regulated and tamoxifen genes are down-regulated. The vast majority of these genes would be excluded from analysis by any combination of statistical procedures currently used for microarray analysis. For instance, a mild restraint of 1.4 fold change and P <0.1 leaves only 5 out of 32 expressed genes on this map (marked as red and blue squares on FIG. 16C), which would essentially eliminate the most differentially affected pathways in these two treatments from the analysis.

For comparison, we identified 477 most effected gene lists by performing conventional ANOVA and t-test (treated vs. untreated animals) on the same two datasets. These genes were mapped onto pathway maps in general data, such as MetaCore™, and statistically significant maps were selected. The highest scored maps were assorted metabolic maps; they displayed certain generic toxic effects such as down-regulation of drug metabolism cytochromes, but no substantial differential expression pattern was observed.

Figure 13:
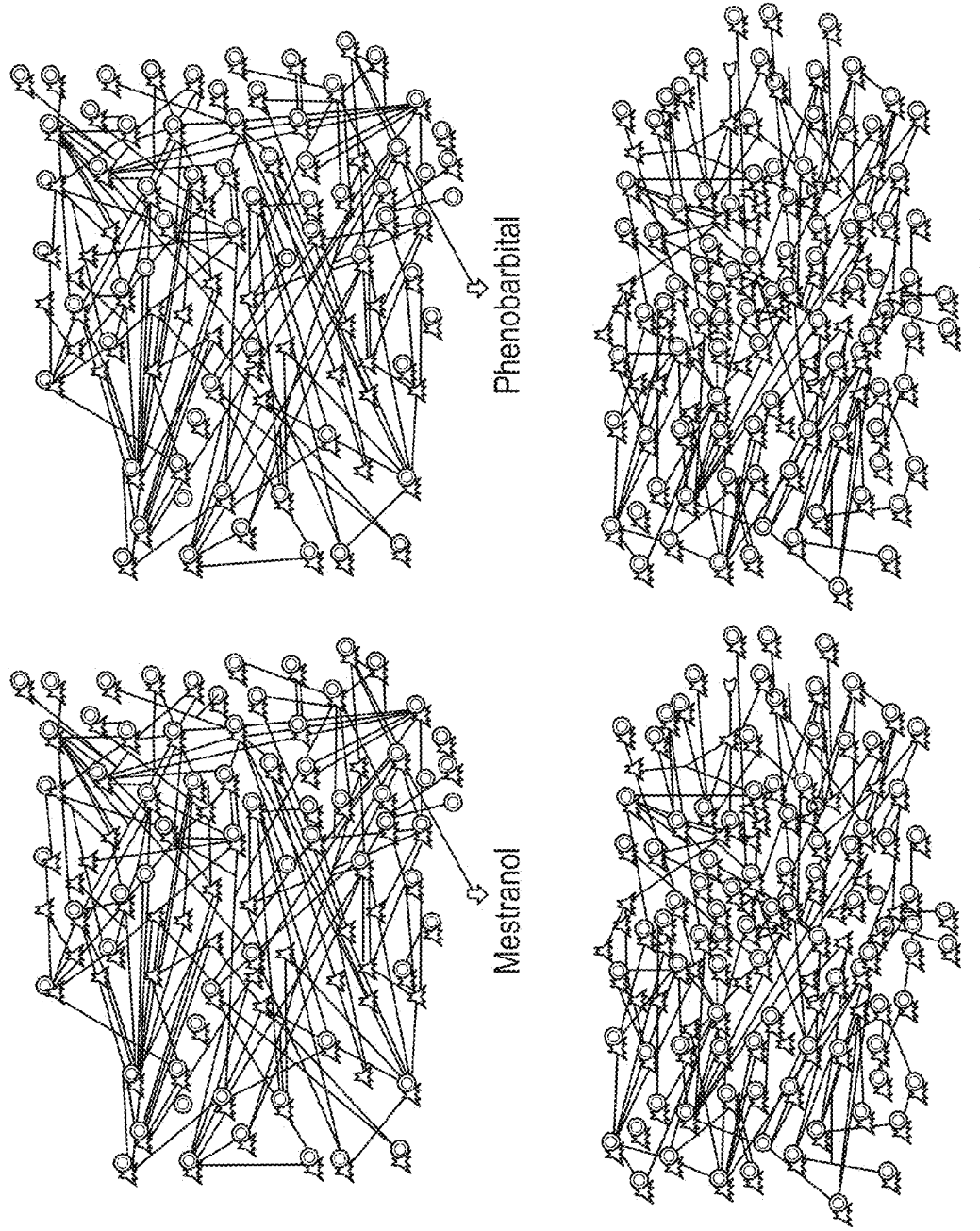
FIG. 13 is a representation of the networks formed by pathways that differentially respond to treatments. The upper panel shows the direct interaction network assembled from the genes from pathways distinguishing between mestranol and phenobarbital treatments. Relative change in expression between treated and untreated rats are mapped (log-ratios, averaged over 5 repeats). In the lower panel, the networks are represented from the genes extracted from pathways differentiating between tamoxifen and phenobarbital. Note that both comparisons contain significant numbers of negatively correlated genes.

FIG. 13 is a representation of the networks formed by pathways that differentially respond to treatments.

Figure 14:
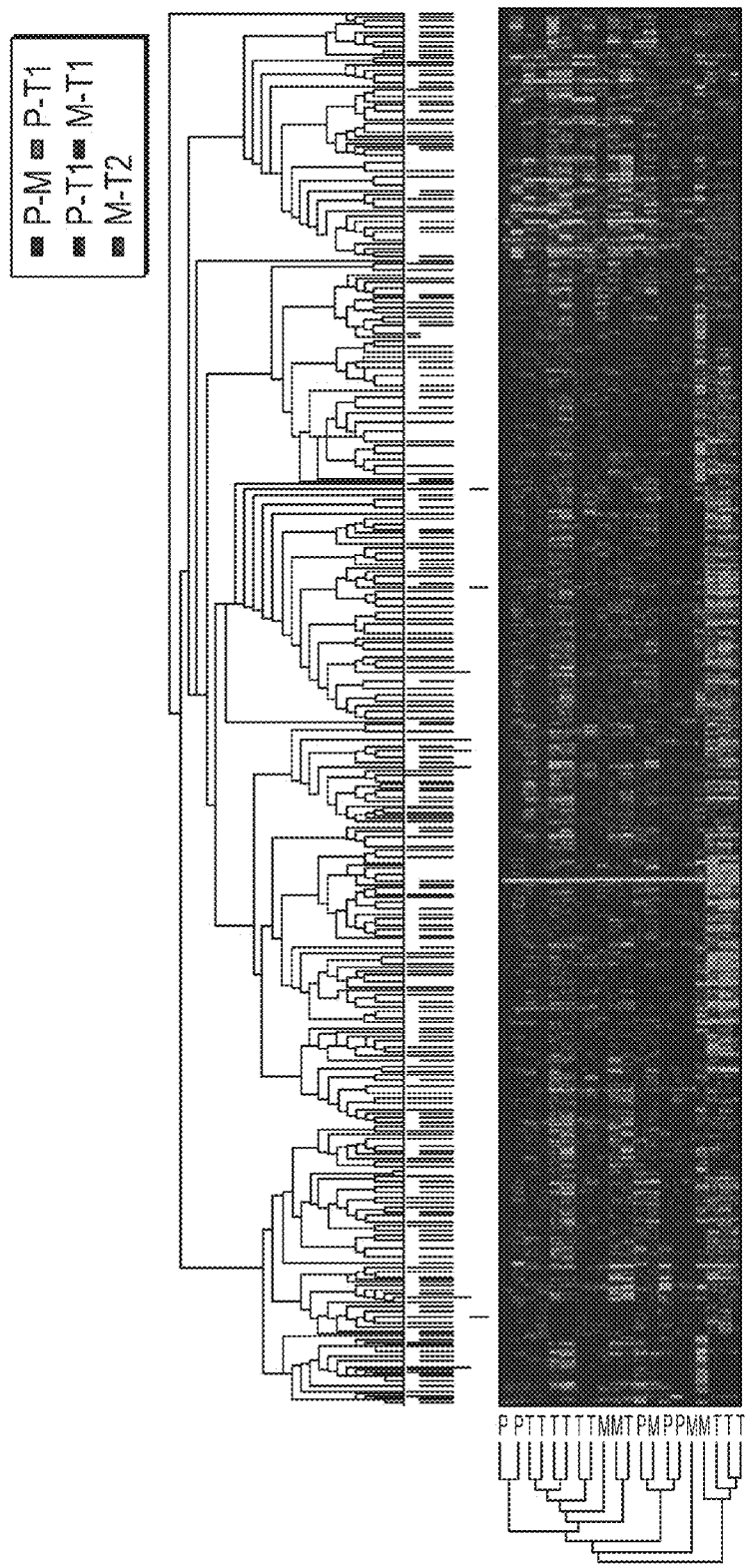
FIG. 14 is a representation of the bi-clustering of the genes which were mapped to pathways.

FIG. 14 is a representation of the bi-clustering of the genes which were mapped to pathways. The bars (red-phenobarbital vs. mestranol, green-phenobarbital vs. tamoxifen (250 nM), blue-phenobarbital vs. tamoxifen (500 nM), black-mestranol vs. tamoxifen (250 nM) and pink-mestranol vs. tamoxifen (500 nM)) mark the genes identified by our method as differentiating between treatments.

Figure 16B:
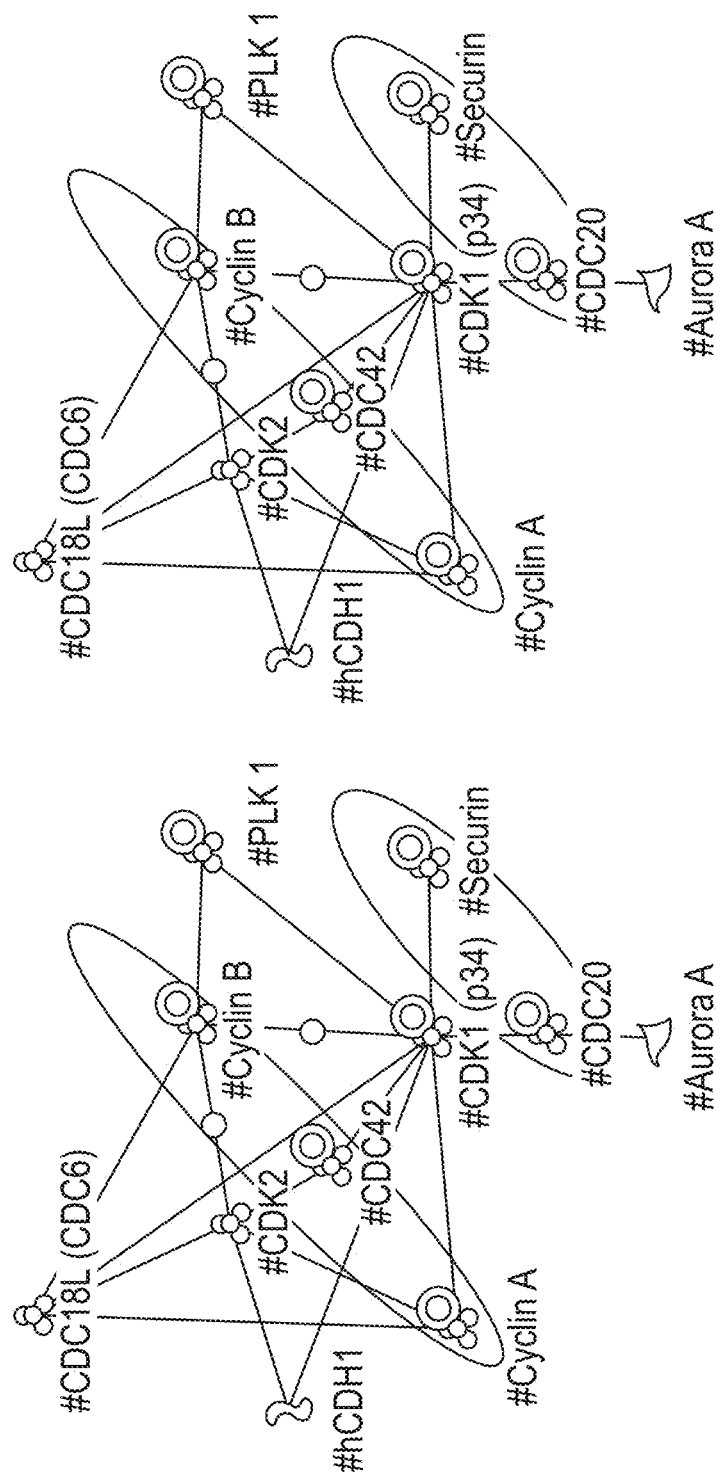
FIG. 16B is a sub-graph from the DI network connecting genes related to mitosis GO process.
Figure 16C:
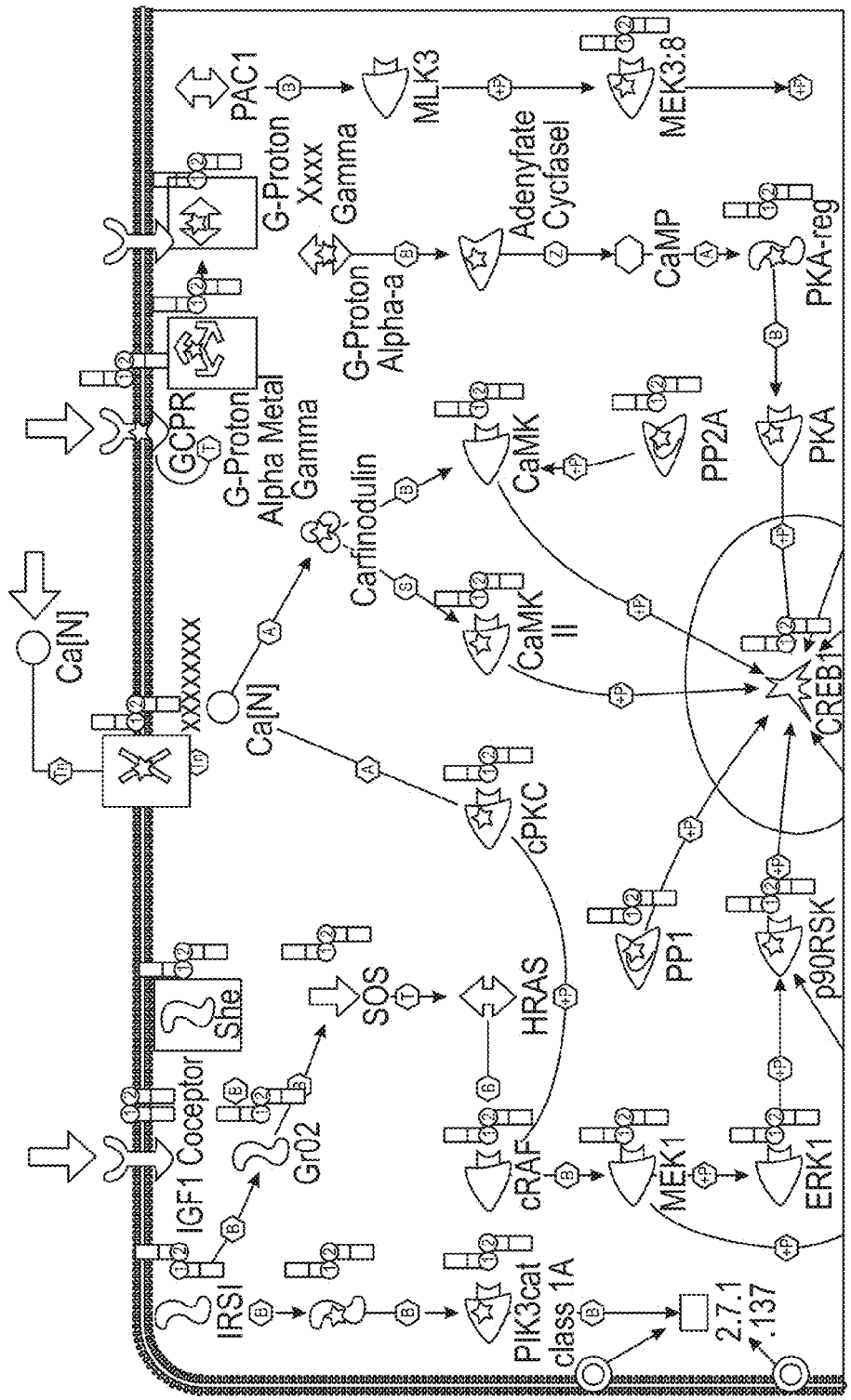
FIG. 16C is the top scored CREB pathway map for the genes content of the network A. Gene expression was mapped without thresholds. The square blocks mark genes in both signature expressed at fold change >1.4 and P<0.1. Red square represents phenobarbital and blue represents tamoxifen at 250 mg/kg. Note that most genes in both sets show high consistency of sign of expression, relative level throughout the pathway, in pre-threshold levels (FC<1.4; P>0.1)

FIG. 16A is a representation of "Direct Interactions" (DI) networks assembled from the genes extracted from the most pathways between tamoxifen and phenobarbital profiles. Blue circles represent down-regulated genes; red circles represent up-regulated genes. FIG. 16B is a sub-graph from the DI network connecting genes related to mitosis GO process. FIG. 16C is the top scored CREB pathway map for the genes content of the network A. Gene expression was mapped without thresholds. The square blocks mark genes in both signature expressed at fold change >1.4 and P<0.1. Red square represents phenobarbital and blue represents tamoxifen at 250 mg/kg. Note that most genes in both sets show high consistency of sign of expression, relative level throughput the pathway, in pre-threshold levels (FC<1.4; P>0.1).

Figure 20A:
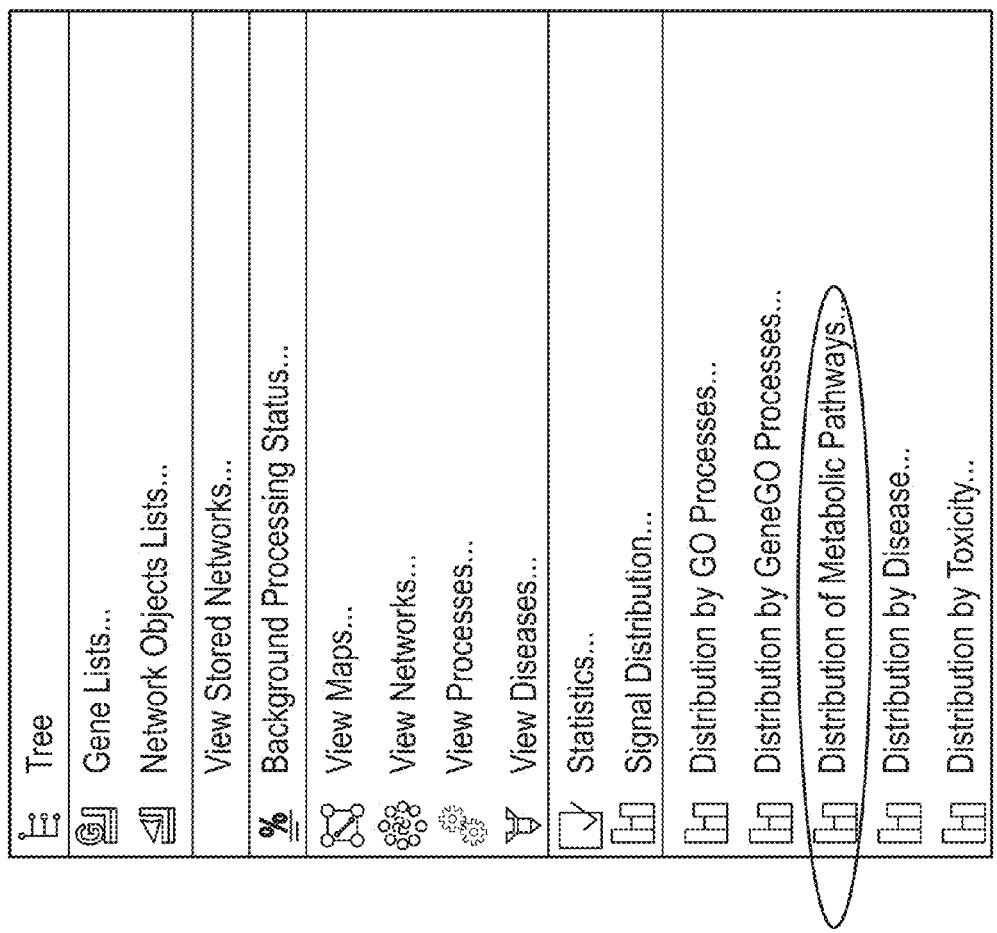
FIG. 20A-C is a representation of the raw data manager interface.
Figure 20B:
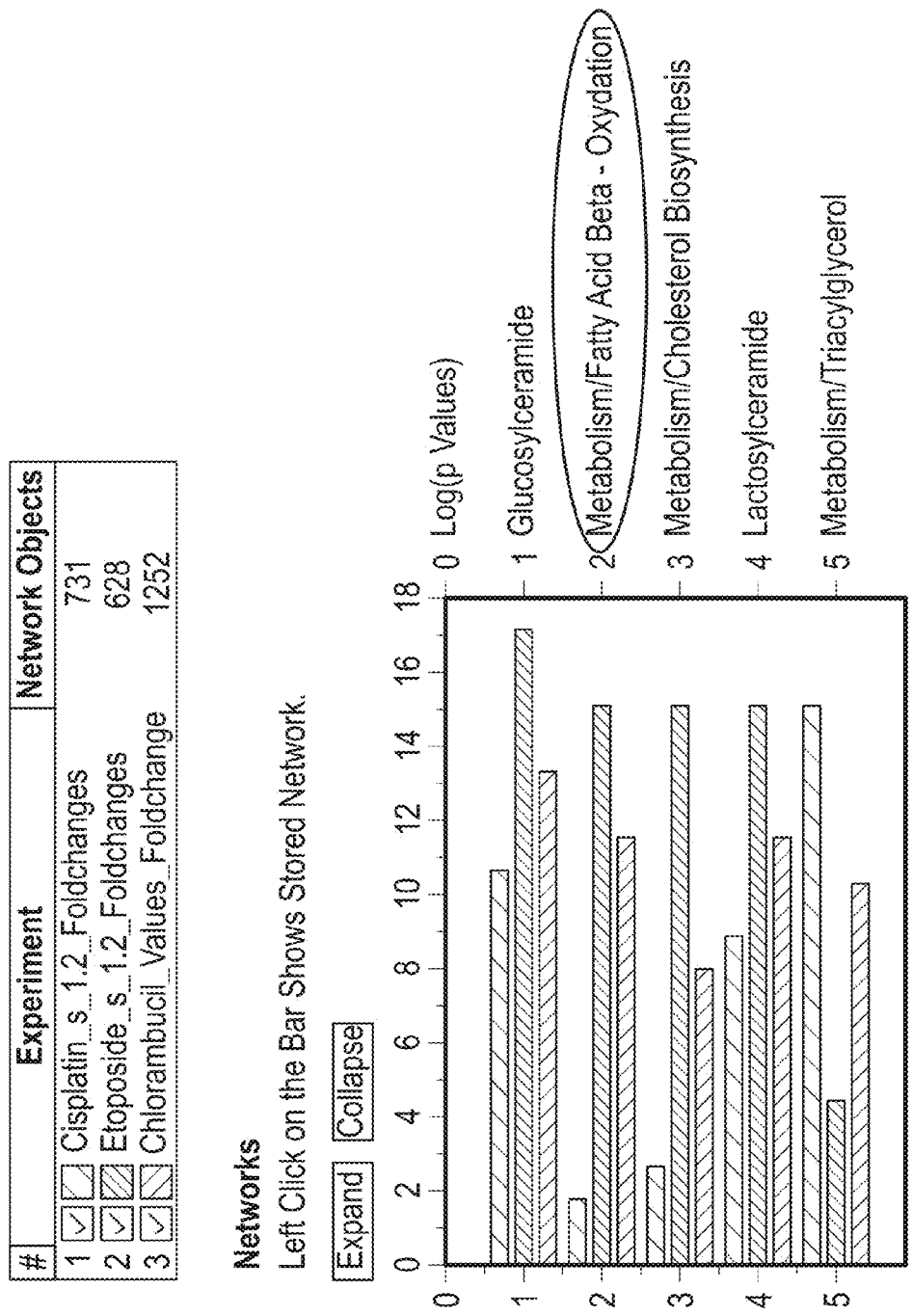
Figure 20C:
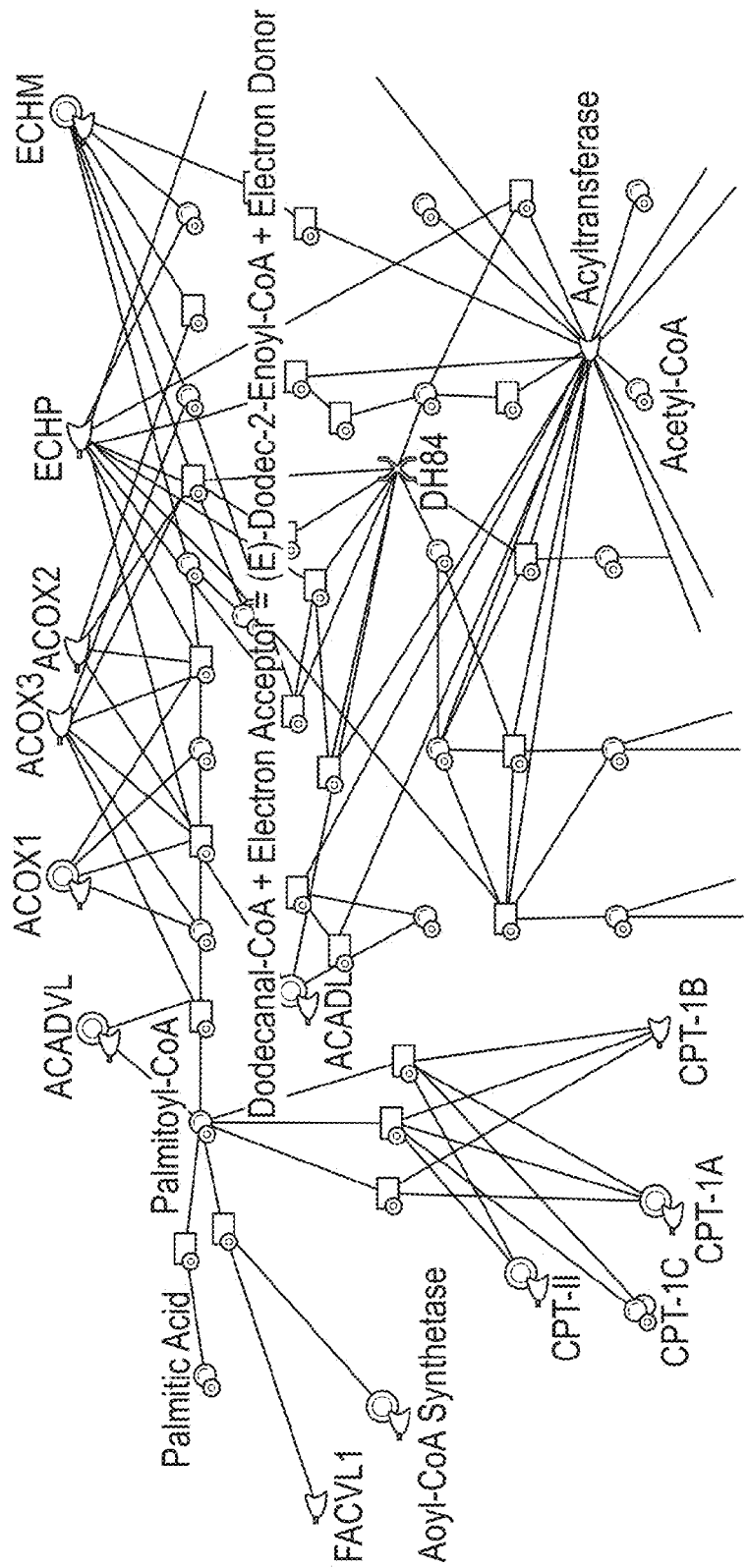

FIG. 20A-C is a representation of a raw data manager interface for a toxicity analysis software module or package. The users will have a standard set of uploaded and processed public data from CEBS, GEO and other sources, and will be able to import internal data and commercial databases. The files are organized in a hierarchical tree view. New files are uploaded via a multi-format parser. The general parser imports microarray, SAGE gene expression, proteomics and siRNA data. Metabolic parser imports experimental metabolic abundance data (CAS numbers, smile strings, brutto formulas). The interactions parser imports custom interactions data (yeast 2 hybrid, pull-down, text associations, etc.).

The workflow for generation of signature networks can be described as follows. First, raw gene expression data are preprocessed by microarray analysis software such as GeneSpring™, Resolver™ or ArrayTrack™, all of which are integrated with a general database, such as MetaCore™. The statistical preprocessing includes data normalization, evaluation of the signal quality (e.g. signal/noise ratio for every gene), calculation of ratio between treated and untreated tissues and ANOVA analysis between repeats for identification of genes that are significantly over-/under-expressed. The resulting data tables are loaded into the general database where expression profiles are concurrently analyzed from multiple treatments. Genes are filtered on their significance (p-value) and fold change. The resulting sets of genes that distinguish treated vs. untreated samples may be mapped using one or more of six major functional analysis tools: canonical pathway maps of cell signaling and metabolism; cellular processes as defined by GO, functional processes defined by GeneGo ontology, disease categories, toxicity categories and pre-set metabolic networks. After the data are mapped, the maps, networks, and categories are ranked based on their statistical significance for the datasets which is calculated as p-values using a hyper-geometric distribution. Maps or processes in common for the majority of treatments in a toxicity category are selected to contribute to a set of signature pathways/networks for this class of toxicants.

The final goal of such a big picture analysis is to identify sets of differentially expressed genes with three properties:

They are functionally well-defined in terms of cellular processes, pathways, or relevance to diseases or toxicities.

They form distinct sub-networks (modules) within the networks.

They are common across multiple treatments. These groups of treatments may or may not correspond to toxicity categories.

Figure 17B:
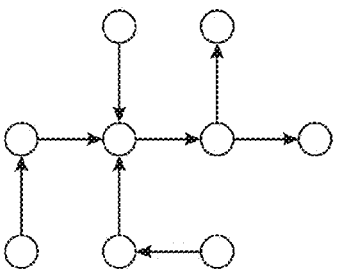

Such modules would then be used as signature networks for this type of toxicity, and expression profiles for new compounds can be benchmarked against them. The requirement that these genes form well-connected network modules is important, as topology-based methods of network analysis may detect similar patterns even when expression profiles are seemingly dissimilar. As represented in FIG. 17B, two gene sets A and B overlap only by two genes. However, they share a significant number of interactions within the same network module. Thus, these two sets have a high degree of functional/mechanistic similarity defined as a set of overlapping, "significant" interactions. An interaction is defined as significant if it has at least one significant gene on its terminus. Moreover, these interactions form a coherent network module that further proves functional relatedness of these two sets. Such similarity is completely undetectable by comparison of gene lists (for instance, gene signatures) for two treatments. These genes may or may not belong to the same functional category.

Figure 17A:
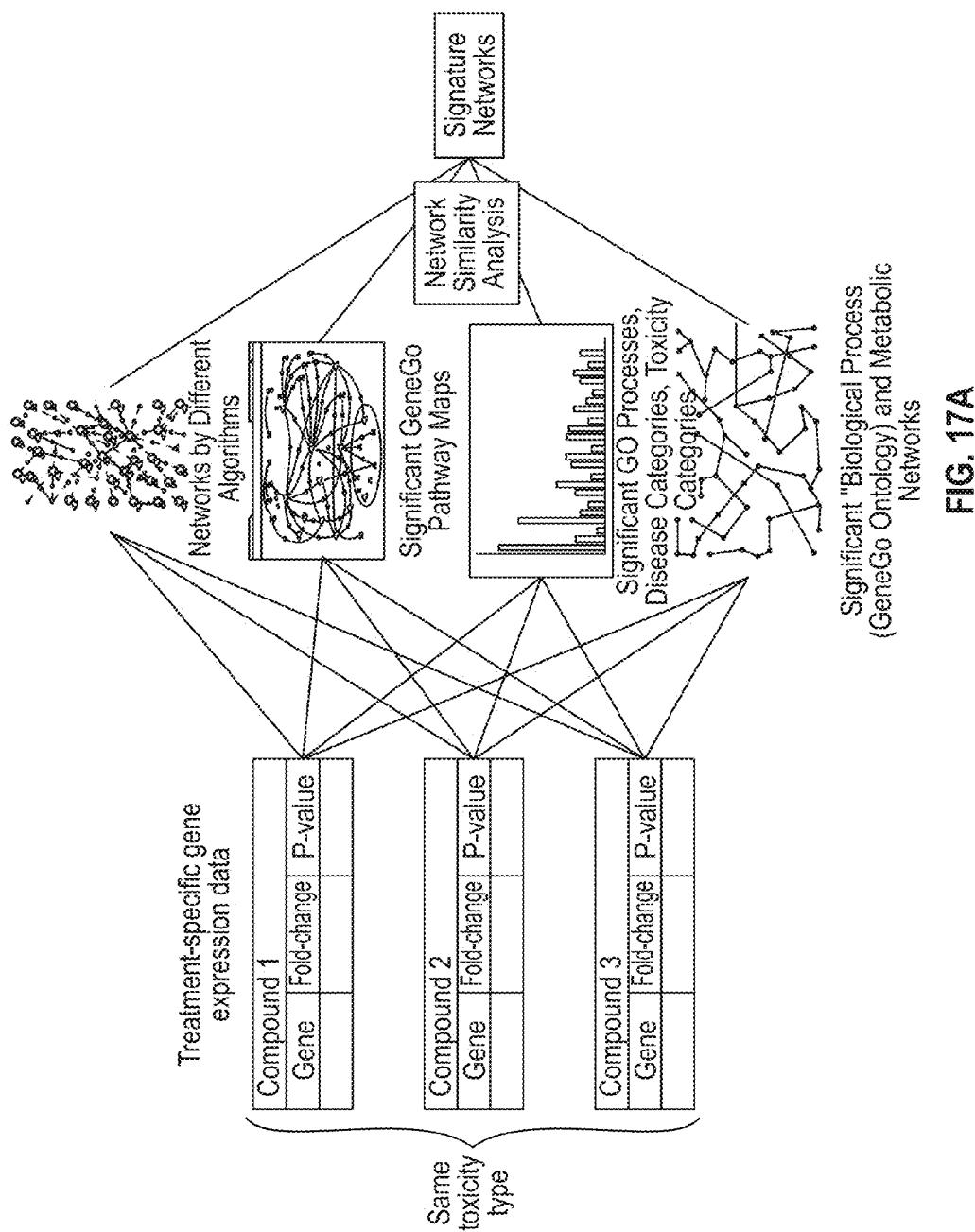
FIG. 17A is a representation of the workflow for generating signature networks from toxicogenomics data. Expression profiles from multiple compounds with similar toxicological profiles are analyzed by different functional filters and common functional categories are selected and networks are built.

FIG. 17A is a representation of the workflow for generating signature networks from toxicogenomics data. Expression profiles from multiple compounds with similar toxicological profiles are analyzed by different functional filters and common functional categories are selected and networks are built. FIG. 17B represents the functional relatedness between gene sets that have little or no direct overlap. Gene sets A (red) and B (green) have two common genes (stripes) but all eight network edges are similar.

In one embodiment of the invention, new criteria for network reconstruction workflow and for developing statistical procedures for quantization of compound response profiles based on network topology and gene content will be developed. This will enable analysis of hundreds of expression profiles in a batch mode and comparison calculations for the entire content of toxicogenomics databases of any size, including CEBS, Tox Express™, DrugMatrix™ and the internal reference databases at drug companies. The module's interface will also feature several parameter options for building custom libraries of signature networks.

The generated networks will substantially overlap and correlate with drug response phenotypes and may or may not correspond to the toxic categories as they exist now (macrophage activators, peroxisome proliferators, genotoxic compounds, etc.). The network comparison can be done on three major levels using the following parameters:

Content comparison—the simplest type that shows what percentage of genes or proteins a set of networks have in common.

Graph comparison—this tool finds the common sub-networks (connected graphs) shared by the set of networks. This is somewhat different from the content comparison as some common nodes may not be a part of such a connected graph.

Global statistical comparison—this tool calculates major statistical properties of the entire network module and compares networks on these properties. These properties include the average distance between nodes, network diameter, network hubs, distribution of node degrees, etc.

Local statistical comparison. Another type of statistics which may be interesting to calculate and compare amongst treatments is the distribution of differentially expressed genes with respect to network neighborhoods of other nodes. This is a novel concept in network comparison and is discussed in further detail below.

The concept of local network statistics as comparison parameters is shown in FIG. 18. For every node on the global network, the neighborhood of the first, second, third, etc. degrees can be built by direct query to the database. The node's interaction neighborhood can be further divided by different parameters such as upstream and downstream interactions; interaction mechanisms (e.g., phosphorylation, binding, covalent modification etc.); transcription factor targets; membrane receptors; kinase-phosphatase pairs, etc. The neighborhood networks will be differentially enriched with expressed genes for different treatment, and the degree of relative enrichment can be evaluated quantitatively.

Statistical significance and its relevance to function is a key issue; it will be assessed using the same procedures as currently used in MetaCore™ on p-value calculations for maps, processes, diseases and toxicities. Essentially, every neighborhood will be represented as a gene subset, and p-values will be calculated as a probability of intersection of a random set of same size with the set of differentially expressed genes for a treatment. Moreover, p-values can be calculated for upstream and downstream components to reveal putative sources and sinks for activated processes. For example, in the network represented in FIG. 18A the nodes upstream of the node X are predominantly under-expressed while those downstream of it are primarily over-expressed. A detailed analysis could reveal a quantitative measure for statistical significance of such overrepresentation. Thus every node in a network will be characterized by a number of local statistical scores (network descriptors) showing potential bias of the distribution of differentially expressed genes among its neighbors. When expression profiles from different treatments are mapped onto networks, the local statistical scores will be compared to aid in assessing their similarity.

FIG. 18 is a representation of a statistically significant network (directed graph) neighborhood. In FIG. 18A, node X features down-regulated upstream first degree neighbors (blue), and up-regulated downstream neighbors. Statistical scores for such distributions can be calculated using hyper-geometric distribution. FIG. 18B represents a real network. Statistically significant distribution of down-regulated genes from allyl-alcohol induced expression profile in the neighborhood of P70 S6 kinase1. Upstream genes are predominantly down-regulated (blue).

Figure 19A:
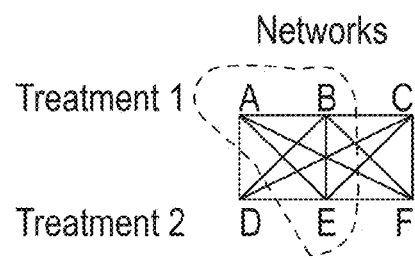
FIG. 19A represents calculation of similarity scores between all networks across multiple treatments.
Figure 19B:
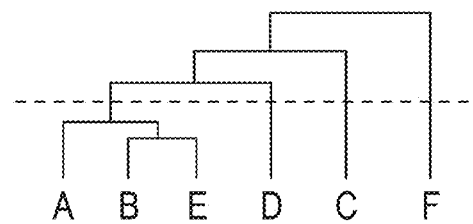
FIG. 19B represents hierarchical clustering for selecting groups of networks most similar between treatments within class.
Figure 19C:
FIG. 19C represents a compound toxicity report matrix.

The networks that display the highest similarity between treatments for a toxicity type will be grouped into the signature set for this type. Statistical tools for scoring the sets of pre-defined pathways and networks may be directly compared for multiple treatments. This means that every network generated by an individual expression profile is to be compared against all other networks for all expression profiles. Based on inter-network distance calculations described above, the network similarity tables will be generated, followed by hierarchical clustering of networks. FIG. 19 is a representation of a comparison of drug treatment signature networks. FIG. 19A represents calculation of similarity scores between all networks across multiple treatments; FIG. 19B represents hierarchical clustering for selecting groups of networks most similar between treatments within class; and FIG. 19C represents a compound toxicity report matrix.

The lower level clusters of the most similar networks will be selected and their composition analyzed. The clusters with significant diversity (70% to 80% of all treatments of the same class) will be chosen as input for generation of treatment-specific signature networks. For instance, networks A, B and E are chosen as the most similar ones on FIG. 19A. Different types of metrics based on different contributions of similarity parameters outlined above will be tested. The treatment-specific networks will then be combined into signature networks for the toxicity class.

According to one aspect of the invention, a software module or package to predict toxicity of compounds may be able to benchmark in-house gene expression profiles against a pre-set collection of signature networks. The sets of significant maps, networks, processes and other functional categories may be calculated from user's drug expression profile that may be compared with the signature network libraries using network similarity tools. Potential toxicity profile for the compound may then be reported as a matrix of the similarity for each network. In user interface, the similarity may be represented both numerically and visually (FIG. 19C). A set of interactive options may enable users to report the matrix by toxicity type.

According to one embodiment of the invention, a software module or package to predict toxicity of compounds may establish standardized toxicogenomics data analysis workflows and reporting and may include raw drug response data from public databases, pre-built networks and pathway maps for the processes relevant for toxcicology, and signature networks and modules characteristic for types of toxicity. The raw toxicogenomics gene expression data will be used for generating signature networks and as a reference. The processed content (pathways, categories and signature networks) may be applied both as a library of functional descriptors, and as a tool for mapping experimental toxicity profiles for novel compounds.

According to another embodiment of the invention, a software module or package to predict toxicity of compounds may have any and all available toxicogenomics datasets (microarray, SAGE, proteomics, metabolomics) imported into its database using existing data parsers with the data then pre-processed (normalization within the experiment, treatment-control ratios, p-value calculations for consistency between samples), annotated, deposited in a tree view in the data manager and used as reference. An intuitive wizard may allow customers to upload and process proprietary databases and cross-analyze public, internal and proprietary databases. Almost any type of complimentary molecular data (proteomics, metabolomics, siRNA assays, high content screening etc.) and custom protein interactions data (yeast 2 hybrid assays, immunoprecipitation pull-down experiments, co-expression etc.) may be imported via a universal parser.

When an experimental dataset is uploaded, its gene content may matched with specialty gene sets already loaded into the general database, and p-values are calculated as a probability of the same number of genes from a random set to match gene identifications within the category. Such p-value distributions for a dataset by functional categories can serve as quantitative descriptors for the dataset, and different drug response profiles can be compared and clustered based on such functional descriptors. The workflow for this initial level of functional analysis is shown on FIGS. 20A and 20B for three rat microarray gene expression profiles in response to cisplatin, etoposide and cisplatin (Johnson & Johnson (J&J) New Brunswick, N.J., data in CEBS). The expression data may also be mapped on the biological networks pre-built by our annotators for signaling and metabolic processes using the gene content of the category folder as an input list. Whenever the gene identifications from the drug response expression file matches the gene identification visualized on the networks, it gets marked with color, and a p-value is calculated for each network (FIG. 20C). The distribution of up- and down-regulated genes on the pre-set networks can be quantified in terms of network topology and also used as a functional descriptor.

A series of networks may be built in a fashion similar to the network for inflammation shown in FIGS. 20A-C. After the toxicity categories are assembled, toxicity networks may be built and integrated into a software module or package to predict toxicity of compounds (FIG. 20A). Each compound file may be mapped on toxicity networks built for toxic categories, and the networks may be compared by p-values and topology-based tools for signature networks. All compound profiles therefore may be catalogued with multiple functional descriptors, and the data stored as reference for evaluation expression profiles for novel compounds.

As the result of this comprehensive study, each compound may be assigned a number of quantitative functional parameters, and the general score(s) for toxicity relevance calculated (Table 5). In order for a compound profile to be assigned with a certain potential toxicity, a number of its functional indicators must be within the range for this type of toxicity. The ranges may be established empirically in the process of analysis of J&J (New Brunswick, N.J.) datasets and other public sources. Based on the final numbers, the total score may be calculated. Instead of or in addition to a total score, a pattern of functional descriptors may be determined for toxicity categorization.

TABLE 5

Matrix of Functional Descriptors for Compound Expression Profiles

| | Map 1 up | Tox. down | Tox. ntwrk1 | GO 1 | Met. Ntwrk | GG ntwrk | edges | Sign ntwrk1 P+/- | AP1 tgt | Tox. matrix Sign. ntwrks | Total |
|---|---|---|---|---|---|---|---|---|---|---|---|
| Cpd1 | score | score | score | score | score | score | score | score | score | score | |
| Cpd2 | score | score | score | score | score | score | score | score | score | score | |
| Cpd3 | score | score | score | score | score | score | score | score | score | score | |
| Cpd4 | score | score | score | score | score | score | score | score | score | score | |
| Cpd5 | score | score | score | score | score | score | score | score | score | score | |
| Cpd6 | score | score | score | score | score | score | score | score | score | score | |
| ... | score | score | score | score | score | score | score | score | score | score | |
| Cpd100 | score | score | score | score | score | score | score | score | score | score | |

Toxicity  type 1  type 2  type 3  type 4

According to an embodiment of the invention, a software module or package to predict toxicity of compounds may be designed as an analytical engine for functional analysis of compound toxicity related data. The software module or package may be neither a universal bioinformatics platform, nor a statistical data analysis package, nor a wet lab data management system but all these tools may be needed for modern high-throughput experimental research and may be requested and used by users of the software module or package. Such tools may include: microarray analysis software; translational medicine/wet lab informatics; proteomics; and metabolomics.

According to an embodiment of the invention, a software module or package to predict toxicity of compounds may be a universal platform for toxicogenomics research, and thus may be able to do data exchange with a variety of modern informatics environments. The three major standards for biological data exchange are SBML, PSI-MI, and BioPax.

According to another embodiment of the invention, a software module or package to predict toxicity of compounds may be able exchange data with third party tools and informatics systems using an API (Application Program Interface) for information exchange.

The system to determine gene clustering and signature networks, and components thereof such as the databases and software tools, may be implemented using software (e.g., C, C#, C++, Java, or a combination thereof), hardware (e.g., one or more application-specific integrated circuits), firmware (e.g., electronically programmed memory), or any combination thereof. One or more of the components of the drug discovery system may reside on a single computer system (e.g., the data mining subsystem), or one or more components may reside on separate, discrete computer systems. Further, each component may be distributed across multiple computer systems, and one or more of the computer systems may be interconnected.

Further, on each of the one or more computer systems that include one or more components of the drug discovery system, each of the components may reside in one or more locations on the computer system. For example, different portions of the components of the drug discovery system may reside in different areas of memory (e.g., RAM, ROM, disk, etc.) on the computer system. Each of such one or more computer systems may include, among other components, a plurality of known components such as one or more processors, a memory system, a disk storage system, one or more network interfaces, and one or more busses or other internal communication links interconnecting the various components.

The system to determine gene clustering and signature networks may be implemented on a computer system described below in relation to FIGS. 21 and 22.

The system described above is merely an illustrative embodiment of a system to determine gene clustering and signature networks. Such an illustrative embodiment is not intended to limit the scope of the invention, as any of numerous other implementations of a system to determine gene clustering and signature networks, for example, variations of the databases contained within, are possible and are intended to fall within the scope of the invention. None of the claims set forth below are intended to be limited to any particular implementation of the system to determine gene clustering and signature networks unless such claim includes a limitation explicitly reciting a particular implementation.

Various embodiments according to the invention may be implemented on one or more computer systems. These computer systems may be, for example, general-purpose computers such as those based on Intel PENTIUM-type processor, Motorola PowerPC, Sun UltraSPARC, Hewlett-Packard PA-RISC processors, or any other type of processor. It should be appreciated that one or more of any type computer system may be used to determine gene clustering and signature networks according to various embodiments of the invention. Further, the software design system may be located on a single computer or may be distributed among a plurality of computers attached by a communications network.

A general-purpose computer system according to one embodiment of the invention is configured to perform any of the described system to determine gene clustering and signature networks functions. It should be appreciated that the system may perform other functions, including network communication, and the invention is not limited to having any particular function or set of functions.

Figure 21:
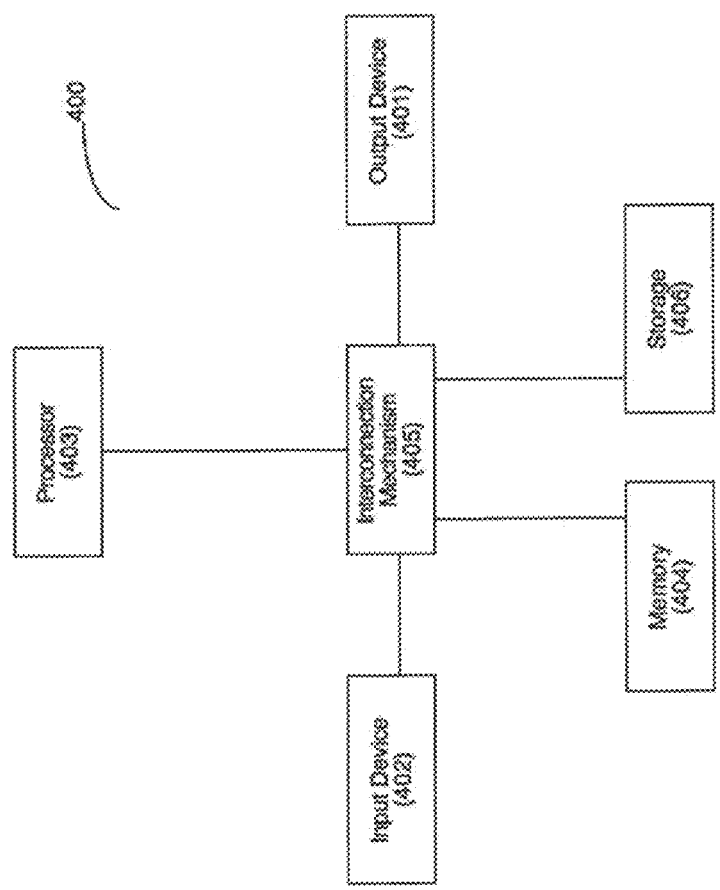
FIG. 21 is a block diagram of a general-purpose computer system upon which various embodiments of the invention may be implemented and FIG. 22 is a block diagram of a computer data storage system with which various embodiments of the invention may be practiced.

For example, various aspects of the invention may be implemented as specialized software executing in a general-purpose computer system 400 such as that shown in FIG. 21. The computer system 400 may include a processor 403 connected to one or more memory devices 404, such as a disk drive, memory, or other device for storing data. Memory 404 is typically used for storing programs and data during operation of the computer system 400. Components of computer system 400 may be coupled by an interconnection mechanism 405, which may include one or more busses (e.g., between components that are integrated within a same machine) and/or a network (e.g., between components that reside on separate discrete machines). The interconnection mechanism 405 enables communications (e.g., data, instructions) to be exchanged between system components of system 400. Computer system 400 also includes one or more input devices 402, for example, a keyboard, mouse, trackball, microphone, touch screen, and one or more output devices 401, for example, a printing device, display screen, speaker. In addition, computer system 400 may contain one or more interfaces (not shown) that connect computer system 400 to a communication network (in addition or as an alternative to the interconnection mechanism 405.

Figure 22:
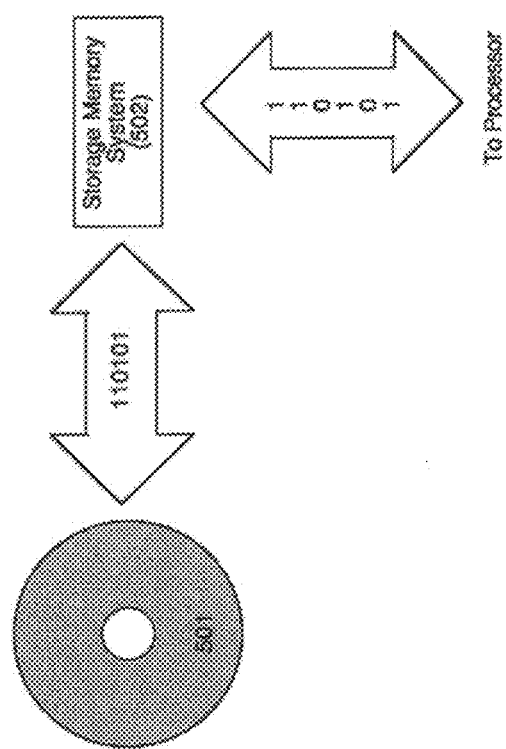

The storage system 406, shown in greater detail in FIG. 22, typically includes a computer readable and writeable nonvolatile recording medium 501 in which signals are stored that define a program to be executed by the processor or information stored on or in the medium 501 to be processed by the program. The medium may, for example, be a disk or flash memory. Typically, in operation, the processor causes data to be read from the nonvolatile recording medium 501 into another memory 502 that allows for faster access to the information by the processor than does the medium 501. This memory 502 is typically a volatile, random access memory such as a dynamic random access memory (DRAM) or static memory (SRAM). It may be located in storage system 406, as shown, or in memory system 404, (not shown). The processor 403 generally manipulates the data within the integrated circuit memory 404, 502 and then copies the data to the medium 501 after processing is completed. A variety of mechanisms are known for managing data movement between the medium 501 and the integrated circuit memory element 404, 502, and the invention is not limited thereto. The invention is not limited to a particular memory system 404 or storage system 406.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

Although computer system 400 is shown by way of example as one type of computer system upon which various aspects of the invention may be practiced, it should be appreciated that aspects of the invention are not limited to being implemented on the computer system as shown in FIG. 21. Various aspects of the invention may be practiced on one or more computers having a different architecture or components than that shown in FIG. 21.

Computer system 400 may be a general-purpose computer system that is programmable using a high-level computer programming language. Computer system 400 may be also implemented using specially programmed, special purpose hardware. In computer system 400, processor 403 is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME) or Windows XP operating systems available from the Microsoft Corporation, MAC OS System X available from Apple Computer, the Solaris Operating System available from Sun Microsystems, or UNIX available from various sources. Many other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that the present invention is not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects of the invention may be performed on a client-server system that includes components distributed among one or more server systems that perform various functions according to various embodiments of the invention. These components may be executable, intermediate (e.g., IL), or interpreted (e.g., Java) code that communicates over a communication network (e.g., the Internet) using a communication protocol (e.g., TCP/IP).

It should be appreciated that the invention is not limited to executing on any particular system or group of systems. Also, it should be appreciated that the invention is not limited to any particular distributed architecture, network, or communication protocol.

Various embodiments of the present invention may be programmed using an object-oriented programming language, such as SmallTalk, Java, C++, Ada, or C# (C-Sharp). Other object-oriented programming languages may also be used. Alternatively, functional, scripting, and/or logical programming languages may be used. Various aspects of the invention may be implemented in a non-programmed environment (e.g., documents created in HTML, XML or other format that, when viewed in a window of a browser program, render aspects of a graphical-user interface (GUI) or perform other functions). Various aspects of the invention may be implemented as programmed or non-programmed elements, or any combination thereof.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

As used herein, whether in the written description or the claims, the terms "comprising", "including", "containing", "characterized by" and the like are to be understood to be open-ended, i.e., to mean including but not limited to. Only the transitional phrases "consisting of" and "consisting essentially of", respectively, shall be closed or semi-closed transitional phrases, as set forth, with respect to claims, in the United States Patent Office Manual of Patent Examining Procedures (Eighth Edition 2$^{nd}$ Revision, May 2004), Section 2111.03.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

We claim:

1. A method for categorizing a breast cancer tissue sample, said method comprising:
   a) providing an article of manufacture, said article comprising oligonucleotides for measuring gene expression of genes in the following descriptor groups:
      (1) PSMD3, TCAP, ERBB2, THRAP4, GRB7, CRK7, GSDML, LENEP, PPARBP;
      (2) DNALI1, XBP1, AR, FOXA1;
      (3) GATA3, TFF3, ACADSB, ESR1, CAl2;
      (4) KRT17, SERPINB5, KRT5, GABRP, ANXA8, TRIM29, S100A2;
      (5) KRT18, KRT8, PPP2CA, KRT8L2;
      (6) COL11A1, WNT2, MMP14, PLAU, PLAUR;
      (7) FN1, THY1, BAPX1, COL5A2;
      (8) PSMB9, STAT1, PDCD1LG2, GBP1, CXCL10, UBE2L6, TAP1, LAP3; and
      (9) CEACAM3, CEACAM5, CEACAM6, CEACAM7,
   said oligonucleotides comprising primer pairs suitable for reverse-transcriptase polymerase chain reaction (RT-PCR) of the genes in the descriptor groups, wherein the primer pairs comprise primers having the sequences of SEQ ID NOs:1-100;
   b) measuring expression of genes of the descriptor groups in the tissue sample using the primer pairs to carry out an RT-PCR amplification of the genes;
   c) assigning a positive or negative status for each of the descriptor groups based on whether a majority of genes in a group are overexpressed in the sample; and
   d) categorizing the breast cancer tissue sample based on a combination of the positive and/or negative statuses so determined,
   wherein SEQ ID NOs:1-100 are:

| Gene | Sense Primer | Antisense Primer |
|---|---|---|
| PSMD3 | TGTGATCACACACTCCCGTT (SEQ ID NO: 1) | TGGACCTGTCTTCCTCTACA (SEQ ID NO: 2) |
| TCAP | GATCATGGCTACCTCAGAGC (SEQ ID NO: 3) | CTGGGAGCTGTTGCTCTCTG (SEQ ID NO: 4) |
| ERBB2 | ACCGCGCCCAGAGTCCTTAGTGAT (SEQ ID NO: 5) | CAGCAGAATGCCAACCACCG (SEQ ID NO: 6) |
| GRB7 | GGAGAAAAAAAACAGAAAGAGC (SEQ ID NO: 7) | TTAACGGAACCAGTTGTGTG (SEQ ID NO: 8) |
| THRAP4 | TCACAAAGGGAGCCACGAGG (SEQ ID NO: 9) | TCTAGCGGCTTCCAGTTCCC (SEQ ID NO: 10) |
| CRK7 | CTAGACACCACTCCTGGCTG (SEQ ID NO: 11) | GTGCTTGCCTGTATTCCTGG (SEQ ID NO: 12) |
| GSDML | TTAACATGCACAACCTGCCA (SEQ ID NO: 13) | TCTCTATCCTGCTGGAGCTG (SEQ ID NO: 14) |
| LENEP | CTTCCTCGGAACTGTTGCCC (SEQ ID NO: 15) | ACCTGAGCGATGCCAGCCAT (SEQ ID NO: 16) |
| PPARBP | CCTCCACAGAGAGGTAACTCCTAA (SEQ ID NO: 17) | GGGGGAGGGAAGATTATTTT (SEQ ID NO: 18) |
| DNALI1 | AGTGCTGGAATTACAGGCTTGTAA (SEQ ID NO: 19) | TCCTGACCTCATGTGATCCA (SEQ ID NO: 20) |
| XBP1 | GCATTGTACCTTTTAATTGC (SEQ ID NO: 21) | GACATGGAATTTATGAATGG (SEQ ID NO: 22) |
| FOXA1 | AAAGTCCTTAACTGCAAATG (SEQ ID NO: 23) | CAGTGTTATGCACTTTCCAC (SEQ ID NO: 24) |
| AR | TTTTCTCTAAAGTTCCCTTC (SEQ ID NO: 25) | CCTGTCTCTTAGAAGGAAAA (SEQ ID NO: 26) |
| ESR1 | AGTTGGCCCAATATAATTTTGC (SEQ ID NO: 27) | CCTGCAGACAAGGGTTATTA (SEQ ID NO: 28) |
| CA12 | GCAGAGGCTGCTTTTGTGAC (SEQ ID NO: 29) | GGATGTCCACAGCTCAGAGT (SEQ ID NO: 30) |

| Gene | Sense Primer | Antisense Primer |
|---|---|---|
| GATA3 | GGCGCCGTCTTGATACTTTC (SEQ ID NO: 31) | CCCCTAGAAAACCTCCAAAA (SEQ ID NO: 32) |
| TFF3 | TCAGGCACGAAGAACTGTCC (SEQ ID NO: 33) | GGGTGGAGAGAGACTGCTCA (SEQ ID NO: 34) |
| ACADSB | GGTGTCAGTGCACTAAAGGC (SEQ ID NO: 35) | CAGGGAAGAATGGAGAAAGA (SEQ ID NO: 36) |
| ANXA8 | TCACTTCACCTTGAAGCCTC (SEQ ID NO: 37) | AGGAACCCTGCATTTTGAAT (SEQ ID NO: 38) |
| SERPINB5 | ATATTTTCTGGGGTAGATAGTC (SEQ ID NO: 39) | TGGAAGACTTCAACTCTATG (SEQ ID NO: 40) |
| TRIM29 | GACAGACCAATGGTTTATTC (SEQ ID NO: 41) | ACACTTTGGCATTCTCTCTG (SEQ ID NO: 42) |
| S100A2 | GACAAAATAAAAGTCAGCAACC (SEQ ID NO: 43) | GCCTTTGAGTTTTGTATTCA (SEQ ID NO: 44) |
| KRT17 | CTCCCCAGATGGGTTATTTGATT (SEQ ID NO: 45) | GACAGCTTTTGGATGAGCAA (SEQ ID NO: 46) |
| KRT5 | TTGAAGCTCTTCCGGGAGGA (SEQ ID NO: 47) | TGGCAGTGGCAGTGGCTATG (SEQ ID NO: 48) |
| GABRP | AAATCAACTACAAGATCCAG (SEQ ID NO: 49) | GGGACTTAAGAACTGATCTG (SEQ ID NO: 50) |
| KRT18 | TGTCTCTTCTCCAACTGTAG (SEQ ID NO: 51) | TACTTGTCTAGCTCCTCTCG (SEQ ID NO: 52) |
| KRT8L2 | TTCAGCAGCCACCCCTACAC (SEQ ID NO: 53) | GGTCTGTGAAGGAGGCAAAC (SEQ ID NO: 54) |
| KRT8 | CTGGGACACCCACCTGCATA (SEQ ID NO: 55) | GAGATCGCCACCTACAGGAA (SEQ ID NO: 56) |
| PPP2CA | TCGGGTGAATGTACATAAGA (SEQ ID NO: 57) | GCAGTTTCTGGTTATGAATA (SEQ ID NO: 58) |
| COL11A1 | GTGGACCAGAGTAGTCACTTAA (SEQ ID NO: 59) | GCACATCCTATGAGTATTGA (SEQ ID NO: 60) |
| PLAU | GAGCCCAGAGAGGAGAGAGA (SEQ ID NO: 61) | TCCCCTGGTGCTGATCAGAG (SEQ ID NO: 62) |
| PLAUR | CCCGGATTGACGCCATTCTC (SEQ ID NO: 63) | AGGCTCCTGGAATCAGGGGT (SEQ ID NO: 64) |
| WNT2 | GAGATAGGAATTTTATTCTCCC (SEQ ID NO: 65) | ATGGTGTGTTGTATCTTTGT (SEQ ID NO: 66) |
| MMP14 | CAGACCCCAGTTCGCCGACTAA (SEQ ID NO: 67) | AAGCTGCTGCTTTGGGCCGA (SEQ ID NO: 68) |
| FN1 | CCTGTTGTATATGAGATGCA (SEQ ID NO: 69) | GGTAAGAATCATCTGCATCT (SEQ ID NO: 70) |
| BAPX1 | GAAAAAATACAGCGAATAGAGC (SEQ ID NO: 71) | AATGTGAATATCCCTGGCCA (SEQ ID NO: 72) |
| COL5A2 | CGGAATAATAATAAAACATTGGGGC (SEQ ID NO: 73) | CCTGCATGGAAAAAGGAAAATAGT (SEQ ID NO: 74) |
| THY1 | AGATTCCAGAGGCTTGGTTT (SEQ ID NO: 75) | TTCTAAGGGAGGCACTTCCT (SEQ ID NO: 76) |
| PSMB9 | TTGCAGTGAGCCCAAGATTG (SEQ ID NO: 77) | CAGCTGAACCAGAGAGTGCA (SEQ ID NO: 78) |
| STAT1 | GGACAGTCCTTTTAATGCCT (SEQ ID NO: 79) | GATCTAGGGGTGATCTTGGG (SEQ ID NO: 80) |
| PDCD1LG2 | CTGGCAATAATGTATATTTATGGGG (SEQ ID NO: 81) | CCACAAAAAAACAACTTGGTGATG (SEQ ID NO: 82) |
| GBP1 | TGCTATAAGAAACATCAACC (SEQ ID NO: 83) | CACATAATGCCAAATACACA (SEQ ID NO: 84) |
| CXCL10 | GTCTTTCTTAATATTTCCAGGAGAG (SEQ ID NO: 85) | CCAAACACATACAGGAAGGT (SEQ ID NO: 86) |
| UBE2L6 | CAGAATTCATCTCTGACTTTAATGG (SEQ ID NO: 87) | GCCACTGATGGGAATATACA (SEQ ID NO: 88) |
| TAP1 | ATAAATATCAAGAACCTACAGGGTG (SEQ ID NO: 89) | TTTCTTCTCTCTGTGGTGGA (SEQ ID NO: 90) |
| LAP3 | TGCCTCATTTAGGTTGTATT (SEQ ID NO: 91) | AATCAAGACTGTGCAAATTC (SEQ ID NO: 92) |
| CEACAM6 | CTCAAGCTCCTCTACAAAGA (SEQ ID NO: 93) | GTGACTTTCCTGTTGTGACC (SEQ ID NO: 94) |
| CEACAM3 | CTGGAGCCCAGGCTCTTTTC (SEQ ID NO: 95) | CCTCCCTCTTATCAATCCCA (SEQ ID NO: 96) |
| CEACAM5 | CAGAGGGAGGAAGGACAGCA (SEQ ID NO: 97) | TCTTCCCTATTCAGGCTCCA (SEQ ID NO: 98) |
| CEACAM7 | GGCTTTTATTTGTGATTCATGAGTC (SEQ ID NO: 99) | TGAAACATGAGGAAGCAGGT (SEQ ID NO: 100) |

\* \* \* \* \*

```
                         SEQUENCE LISTING

<160> NUMBER OF SEQ ID NOS: 100

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tgtgatcaca cactcccgtt                                                  20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tggacctgtc ttcctctaca                                                  20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gatcatggct acctcagagc                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctgggagctg ttgctctctg                                                  20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
accgcgccca gagtccttag tgat                                             24

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
```

-continued

```
cagcagaatg ccaaccaccg                                               20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ggagaaaaaa aacagaaaga gc                                            22

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ttaacggaac cagttgtgtg                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tcacaaaggg agccacgagg                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tctagcggct tccagttccc                                               20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctagacacca ctcctggctg                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtgcttgcct gtattcctgg                                               20

<210> SEQ ID NO 13
<211> LENGTH: 20
<212> TYPE: DNA
```

```
<213> ORGANISM: Artificial Sequence
<220> FEATURE:
<223> OTHER INFORMATION: Primer

<400> SEQUENCE: 13
ttaacatgca caacctgcca                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tctctatcct gctggagctg                                                 20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cttcctcgga actgttgccc                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
acctgagcga tgccagccat                                                 20

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cctccacaga gaggtaactc ctaa                                            24

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gggggaggga agattatttt                                                 20

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
agtgctggaa ttacaggctt gtaa                                            24
```

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tcctgacctc atgtgatcca                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gcattgtacc ttttaattgc                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gacatggaat ttatgaatgg                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
aaagtcctta actgcaaatg                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cagtgttatg cactttccac                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ttttctctaa agttcccttc                                              20

<210> SEQ ID NO 26
<211> LENGTH: 20
<212> TYPE: DNA
<213> ORGANISM: Artificial Sequence
<220> FEATURE:

<223> OTHER INFORMATION: Primer

<400> SEQUENCE: 26
cctgtctctt agaaggaaaa                                               20

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
agttggccca atataatttt gc                                            22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cctgcagaca agggttatta                                               20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gcagaggctg cttttgtgac                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ggatgtccac agctcagagt                                               20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ggcgccgtct tgatactttc                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
cccctagaaa acctccaaaa                                               20

-continued

```
<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tcaggcacga agaactgtcc                                               20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gggtggagag agactgctca                                               20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggtgtcagtg cactaaaggc                                               20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cagggaagaa tggagaaaga                                               20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tcacttcacc ttgaagcctc                                               20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aggaaccctg cattttgaat                                               20

<210> SEQ ID NO 39
<211> LENGTH: 22
<212> TYPE: DNA
<213> ORGANISM: Artificial Sequence
<220> FEATURE:
<223> OTHER INFORMATION: Primer
```

<400> SEQUENCE: 39
atattttctg gggtagatag tc                                                22

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tggaagactt caactctatg                                                   20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
gacagaccaa tggtttattc                                                   20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
acactttggc attctctctg                                                   20

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
gacaaaataa aagtcagcaa cc                                                22

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gcctttgagt tttgtattca                                                   20

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ctccccagat gggttatttg att                                               23

<210> SEQ ID NO 46
<211> LENGTH: 20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 46
gacagctttt ggatgagcaa    20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ttgaagctct tccgggagga    20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
tggcagtggc agtggctatg    20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
aaatcaacta caagatccag    20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gggacttaag aactgatctg    20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
tgtctcttct ccaactgtag    20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tacttgtcta gctcctctcg                                              20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
ttcagcagcc acccctacac                                              20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
ggtctgtgaa ggaggcaaac                                              20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ctgggacacc cacctgcata                                              20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
gagatcgcca cctacaggaa                                              20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tcgggtgaat gtacataaga                                              20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
gcagtttctg gttatgaata                                              20

<210> SEQ ID NO 59
<211> LENGTH: 22
<212> TYPE: DNA
<213> ORGANISM: Artificial Sequence

```
<220> FEATURE:
<223> OTHER INFORMATION: Primer

<400> SEQUENCE: 59
gtggaccaga gtagtcactt aa                                              22

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gcacatccta tgagtattga                                                 20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gagcccagag aggagagaga                                                 20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
tcccctggtg ctgatcagag                                                 20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
cccggattga cgccattctc                                                 20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
aggctcctgg aatcaggggt                                                 20

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
gagataggaa ttttattctc cc                                              22
```

```
<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
atggtgtgtt gtatctttgt                                              20

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
cagaccccag ttcgccgact aa                                           22

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
aagctgctgc tttgggccga                                              20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
cctgttgtat atgagatgca                                              20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
ggtaagaatc atctgcatct                                              20

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
gaaaaaatac agcgaataga gc                                           22

<210> SEQ ID NO 72
<211> LENGTH: 20
<212> TYPE: DNA
<213> ORGANISM: Artificial Sequence
<220> FEATURE:
<223> OTHER INFORMATION: Primer
```

```
<400> SEQUENCE: 72
aatgtgaata tccctggcca                                              20

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
cggaataata ataaaacatt ggggc                                        25

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
cctgcatgga aaaggaaaa tagt                                          24

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
agattccaga ggcttggttt                                              20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ttctaaggga ggcacttcct                                              20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
ttgcagtgag cccaagattg                                              20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
cagctgaacc agagagtgca                                              20

<210> SEQ ID NO 79
```

```
<211> LENGTH: 20
<212> TYPE: DNA
<213> ORGANISM: Artificial Sequence
<220> FEATURE:
<223> OTHER INFORMATION: Primer

<400> SEQUENCE: 79
ggacagtcct tttaatgcct                                              20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
gatctagggg tgatcttggg                                              20

<210> SEQ ID NO 81
<211> LENGTH: 25
<212> TYPE: DNA
<213> ORGANISM: Artificial Sequence
<220> FEATURE:
<223> OTHER INFORMATION: Primer

<400> SEQUENCE: 81
ctggcaataa tgtatattta tgggg                                        25

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
ccacaaaaaa acaacttggt gatg                                         24

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
tgctataaga aacatcaacc                                              20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
cacataatgc caaatacaca                                              20

<210> SEQ ID NO 85
<211> LENGTH: 25
<212> TYPE: DNA
<213> ORGANISM: Artificial Sequence
<220> FEATURE:
<223> OTHER INFORMATION: Primer

<400> SEQUENCE: 85
```

```
gtctttctta atatttccag gagag                                              25

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
ccaaacacat acaggaaggt                                                    20

<210> SEQ ID NO 87
<211> LENGTH: 25
<212> TYPE: DNA
<213> ORGANISM: Artificial Sequence
<220> FEATURE:
<223> OTHER INFORMATION: Primer

<400> SEQUENCE: 87
cagaattcat ctctgacttt aatgg                                              25

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
gccactgatg ggaatataca                                                    20

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
ataaatatca agaacctaca gggtc                                              25

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
tttcttctct ctgtggtgga                                                    20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
tgcctcattt aggttgtatt                                                    20

<210> SEQ ID NO 92
<211> LENGTH: 20
<212> TYPE: DNA
```

```
<213> ORGANISM: Artificial Sequence
<220> FEATURE:
<223> OTHER INFORMATION: Primer

<400> SEQUENCE: 92
aatcaagact gtgcaaattc                                              20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
ctcaagctcc tctacaaaga                                              20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
gtgactttcc tgttgtgacc                                              20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
ctggagccca ggctcttttc                                              20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
cctccctctt atcaatccca                                              20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
cagagggagg aaggacagca                                              20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
tcttccctat tcaggctcca                                              20
```

```
<210> SEQ ID NO 99
<211> LENGTH: 25
<212> TYPE: DNA
<213> ORGANISM: Artificial Sequence
<220> FEATURE:
<223> OTHER INFORMATION: Primer

<400> SEQUENCE: 99
ggcttttatt tgtgattcat gagtc                                           25

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
tgaaacatga ggaagcaggt                                                 20
```